(12) United States Patent
Karin et al.

(10) Patent No.: US 7,695,921 B2
(45) Date of Patent: Apr. 13, 2010

(54) METHOD FOR DETECTING THE PRESENCE OF PROSTATE CANCER

(75) Inventors: Michael Karin, La Jolla, CA (US); Jun-Li Luo, Jupiter, FL (US); Wei Tan, Calzada, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 12/004,696

(22) Filed: Dec. 21, 2007

(65) Prior Publication Data

US 2008/0227115 A1 Sep. 18, 2008

Related U.S. Application Data

(60) Provisional application No. 60/876,743, filed on Dec. 21, 2006.

(51) Int. Cl.
*G01N 33/53* (2006.01)
*C07K 14/00* (2006.01)
(52) U.S. Cl. .................. 435/7.1; 435/7.21; 435/7.23; 530/350

(58) Field of Classification Search .................. None
See application file for complete search history.

(56) References Cited

OTHER PUBLICATIONS

The National Cancer Institute (What You Need To Know About Prostate Cancer, Sep. 2008).*
Pierson et al. (The Prostate 2002 53:255-262).*
Tockman et al. (Cancer Res., 1992, 52:2711s-2718s).*
Taber's Cyclopedic Medical Dictionary (1985, F.A. Davis Company, Philadelphia, p. 274).*
Busken, C et al. (Digestive Disease Week Abstracts and Itinerary Planner, 2003, abstract No. 850).*
Charalambous et al. (British J. of Cancer, 2003, 88: 1598-1604).*
Luo et al. (Nature Apr. 5, 2007, 446: 690-694).*
Sil et al. (Nature Apr. 8, 2004, 428: 660-664).*

* cited by examiner

*Primary Examiner*—Peter J Reddig
(74) *Attorney, Agent, or Firm*—Medlen & Carroll, LLP

(57) ABSTRACT

The present invention relates to compositions and methods for cancer diagnosis, treatment and drug screening. In particular, the present invention provides compositions and methods for targeting the nuclear translocation of IkB kinase-α (IKKα) and the IKKα-mediated suppression of Maspin expression observed in metastatic prostate cancer cells.

7 Claims, 18 Drawing Sheets

Fig. 3
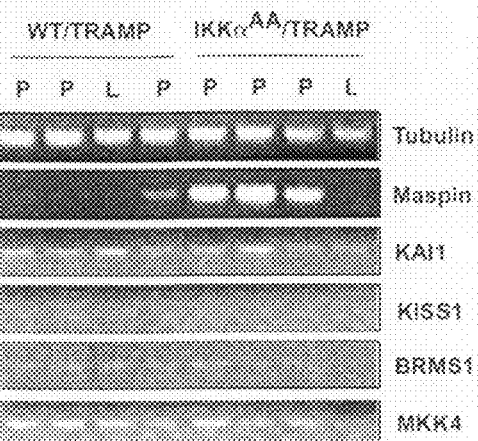
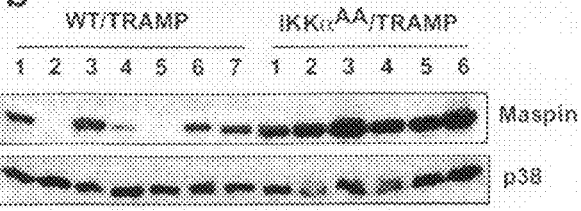
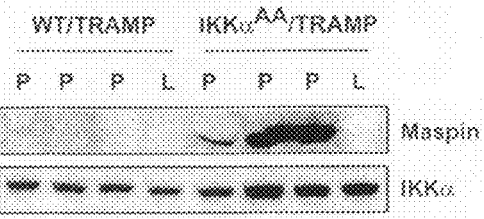
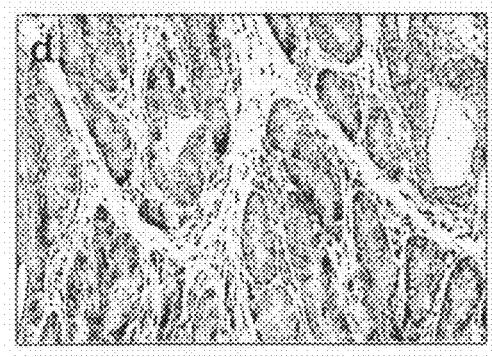
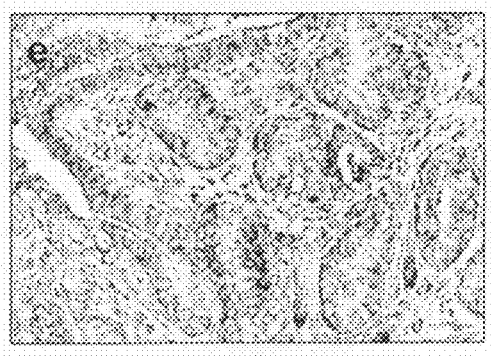

Fig. 5
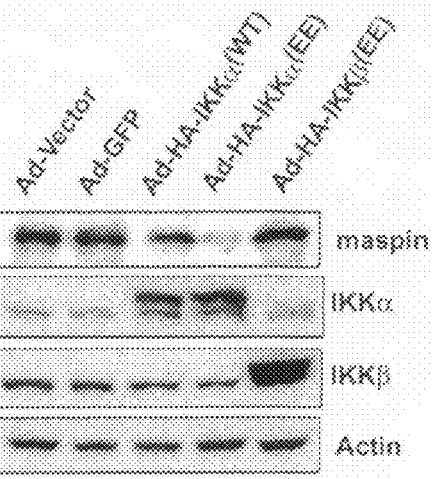
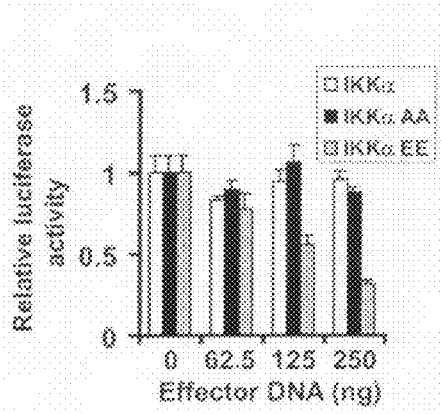
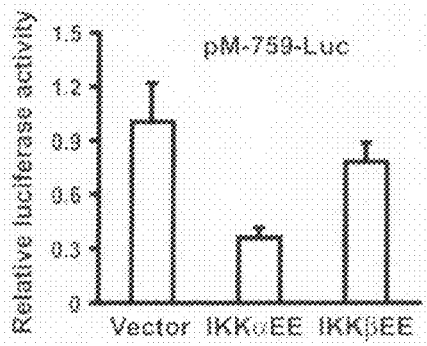
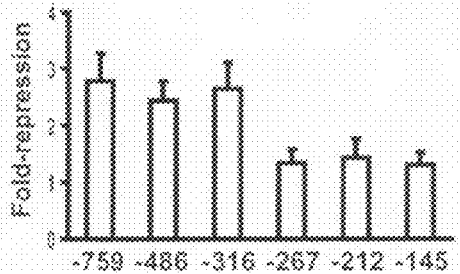
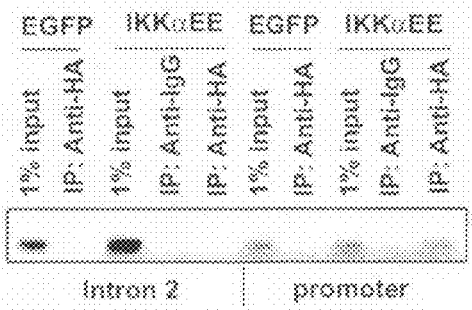

FIG. 14
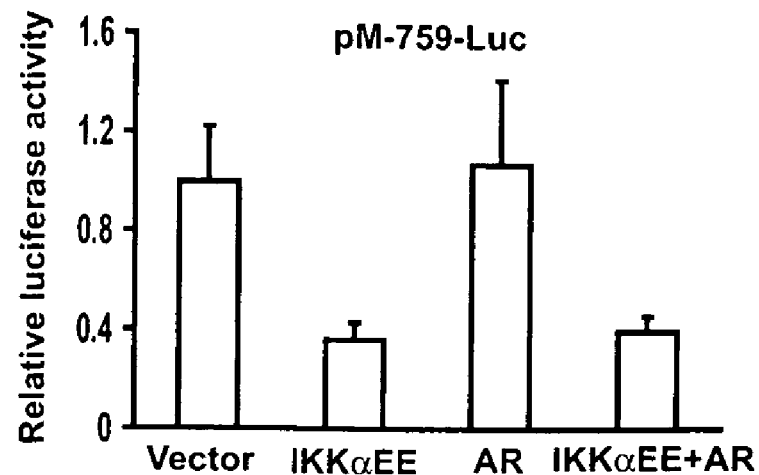
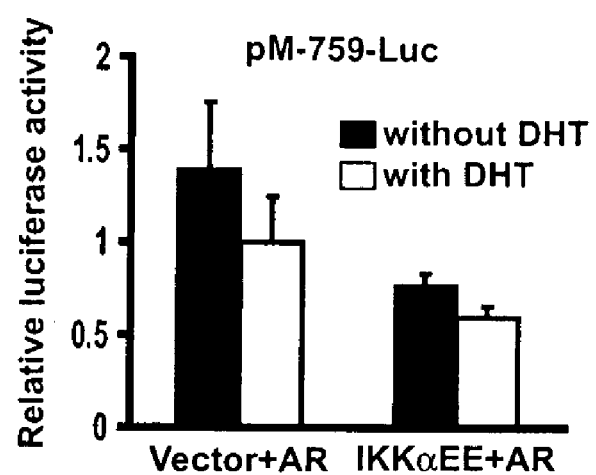
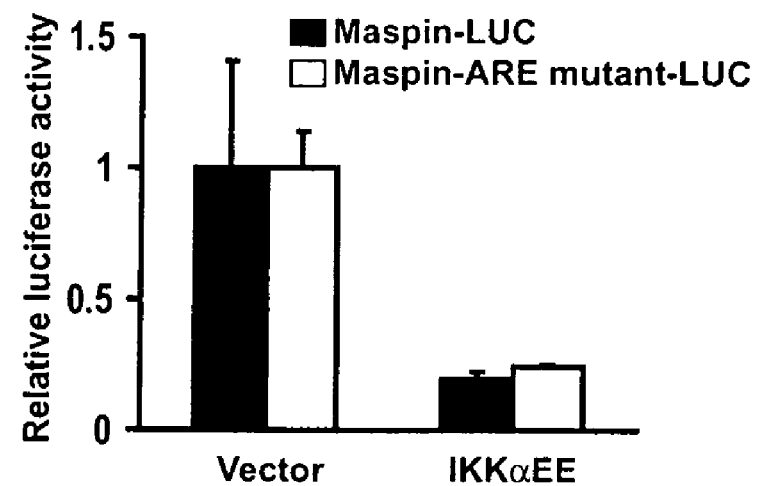

FIG. 16A - IKKα (SEQ ID NO:7)

```
   1 tcgacggaac ctgaggccgc ttgccctccc gccccatgga gcggcccccg gggctgcggc
  61 cgggcgcggg cgggccctgg gagatgcggg agcggctggg caccggcggc ttcgggaacg
 121 tctgtctgta ccagcatcgg gaacttgatc tcaaaatagc aattaagtct tgtcgcctag
 181 agctaagtac caaaaacaga gaacgatggt gccatgaaat ccagattatg aagaagttga
 241 accatgccaa tgttgtaaag gcctgtgatg ttcctgaaga attgaatatt ttgattcatg
 301 atgtgcctct tctagcaatg gaatactgtt ctggaggaga tctccgaaag ctgctcaaca
 361 aaccagaaaa ttgttgtgga cttaaagaaa gccagatact ttctttacta agtgatatag
 421 ggtctgggat tcgatatttg catgaaaaca aaattataca tcgagatcta aaacctgaaa
 481 acatagttct tcaggatgtt ggtggaaaga taatacataa aataattgat ctgggatatg
 541 ccaaagatgt tgatcaagga agtctgtgta catcttttgt gggaacactg cagtatctgg
 601 ccccagagct ctttgagaat aagccttaca cagccactgt tgattattgg agctttggga
 661 ccatggtatt tgaatgtatt gctggatata ggccttttt gcatcatctg cagccattta
 721 cctggcatga aagattaag aagaaggatc caaagtgtat atttgcatgt gaagagatgt
 781 caggagaagt tcggtttagt agccatttac ctcaaccaaa tagcctttgt agtttaatag
 841 tagaacccat ggaaaactgg ctacagttga tgttgaattg ggaccctcag cagagaggag
 901 gacctgttga ccttactttg aagcagccaa gatgtttgt attaatggat cacattttga
 961 atttgaagat agtacacatc ctaaatatga cttctgcaaa gataatttct tttctgttac
1021 cacctgatga agtcttcat tcactacagt ctcgtattga gcgtgaaact ggaataaata
1081 ctggttctca agaacttctt tcagagacag gaatttctct ggatcctcgg aaaccagcct
1141 ctcaatgtgt tctagatgga gttagaggct gtgatagcta tatggtttat ttgtttgata
1201 aaagtaaaac tgtatatgaa gggccatttg cttccagaag tttatctgat tgtgtaaatt
1261 atattgtaca ggacagcaaa atacagcttc caattataca gctgcgtaaa gtgtgggctg
1321 aagcagtgca ctatgtgtct ggactaaaag aagactatag caggctcttt cagggacaaa
1381 gggcagcaat gttaagtctt cttagatata tgctaactt aacaaaaatg aagaacactt
1441 tgatctcagc atcacaacaa ctgaaagcta aattggagtt ttttcacaaa agcattcagc
1501 ttgacttgga gagatacagc gagcagatga cgtatgggat atcttcagaa aaaatgctaa
1561 aagcatggaa agaaatggaa gaaaaggcca tccactatgc tgaggttggt gtcattggat
1621 acctggagga tcagattatg tctttgcatg ctgaaatcat ggggctacag aagagcccct
1681 atggaagacg tcagggagac ttgatggaat ctctggaaca gcgtgccatt gatctatata
1741 agcagttaaa acacagacct tcagatcact cctacagtga cagcacagag atggtgaaaa
1801 tcattgtgca cactgtgcag agtcaggacc gtgtgctcaa ggagctgttt ggtcatttga
1861 gcaagttgtt gggctgtaag cagaagatta ttgatctact ccctaaggtg gaagtggccc
1921 tcagtaatat caaagaagct gacaatactg tcatgttcat gcagggaaaa aggcagaaag
1981 aaatatggca tctccttaaa attgcctgta cacagagttc tgcccgctct cttgtaggat
2041 ccagtctaga aggtgcagta acccctcaga catcagcatg gctgccccg acttcagcag
2101 aacatgatca ttctctgtca tgtgtggtaa ctcctcaaga tggggagact tcagcacaaa
2161 tgatagaaga aaatttgaac tgccttggcc atttaagcac tattattcat gaggcaaatg
2221 aggaacaggg caatagtatg atgaatcttg attggagttg gttaacagaa tga
```

FIG. 16B - IKKα (SEQ ID NO:8)

```
  1 MERPPGLRPG AGGPWEMRER LGTGGFGNVC LYQHRELDLK IAIKSCRLEL STKNRERWCH
 61 EIQIMKKLNH ANVVKACDVP EELNILIHDV PLLAMEYCSG GDLRKLLNKP ENCCGLKESQ
121 ILSLLSDIGS GIRYLHENKI IHRDLKPENI VLQDVGGKII HKIIDLGYAK DVDQGSLCTS
181 FVGTLQYLAP ELFENKPYTA TVDYWSFGTM VFECIAGYRP FLHHLQPFTW HEKIKKKDPK
241 CIFACEEMSG EVRFSSHLPQ PNSLCSLIVE PMENWLQLML NWDPQQRGGP VDLTLKQPRC
301 FVLMDHILNL KIVHILNMTS AKIISFLLPP DESLHSLQSR IERETGINTG SQELLSETGI
361 SLDPRKPASQ CVLDGVRGCD SYMVYLFDKS KTVYEGPFAS RSLSDCVNYI VQDSKIQLPI
421 IQLRKVWAEA VHYVSGLKED YSRLFQGQRA AMLSLLRYNA NLTKMKNTLI SASQQLKAKL
481 EFFHKSIQLD LERYSEQMTY GISSEKMLKA WKEMEEKAIH YAEVGVIGYL EDQIMSLHAE
541 IMGLQKSPYG RRQGDLMESL EQRAIDLYKQ LKHRPSDHSY SDSTEMVKII VHTVQSDRV
601 LKELFGHLSK LLGCKQKIID LLPKVEVALS NIKEADNTVM FMQGKRQKEI WHLLKIACTQ
661 SSARSLVGSS LEGAVTPQTS AWLPPTSAEH DHSLSCVVTP QDGETSAQMI EENLNCLGHL
721 STIHEANEE QGNSMMNLDW SWLTE
```

FIG. 17A - maspin/serpinb5 (SEQ ID NO:9)
```
   1 atggatgccc tgcaactagc aaattcggct tttgccgttg atctgttcaa acaactatgt
  61 gaaaaggagc cactgggcaa tgtcctcttc tctccaatct gtctctccac ctctctgtca
 121 cttgctcaag tgggtgctaa aggtgacact gcaaatgaaa ttggacaggt tcttcatttt
 181 gaaaatgtca aagatatacc ctttggattt caaacagtaa catcggatgt aaacaaactt
 241 agttcctttt actcactgaa actaatcaag cggctctacg tagacaaatc tctgaatctt
 301 tctacagagt tcatcagctc tacgaagaga ccctatgcaa aggaattgga aactgttgac
 361 ttcaaagata aattggaaga aacgaaaggt cagatcaaca actcaattaa ggatctcaca
 421 gatggccact tgagaacat tttagctgac aacagtgtga acgaccagac aaaatcctt
 481 gtggttaatg ctgcctactt tgttggcaag tggatgaaga aatttcctga atcagaaaca
 541 aaagaatgtc ctttcagact caacaagaca gacaccaaac cagtgcagat gatgaacatg
 601 gaggccacgt tctgtatggg aaacattgac agtatcaatt gtaagatcat agagcttcct
 661 tttcaaaata agcatctcag catgttcatc ctactaccca aggatgtgga ggatgagtcc
 721 acaggcttgg agaagattga aaaacaactc aactcagagt cactgtcaca gtggactaat
 781 cccagcacca tggccaatgc caaggtcaaa ctctccattc caaaatttaa ggtggaaaag
 841 atgattgatc ccaaggcttg tctggaaaat ctagggctga acatatctt cagtgaagac
 901 acatctgatt tctctggaat gtcagagacc aagggagtgg ccctatcaaa tgttatccac
 961 aaagtgtgct tagaaataac tgaagatggt ggggattcca tagaggtgcc aggagcacgg
1021 atcctgcagc acaaggatga attgaatgct gaccatccct ttatttacat catcaggcac
1081 aacaaaactc gaaacatcat tttctttggc aaattctgtt ctccttaa
```

FIG. 17B - Maspin /Serpinb5 (SEQ ID NO:10)
```
   1 MDALQLANSA FAVDLFKQLC EKEPLGNVLF SPICLSTSLS LAQVGAKGDT ANEIGQVLHF
  61 ENVKDIPFGF QTVTSDVNKL SSFYSLKLIK RLYVDKSLNL STEFISSTKR PYAKELETVD
 121 FKDKLEETKG QINNSIKDLT DGHFENILAD NSVNDQTKIL VVNAAYFVGK WMKKFPESET
 181 KECPFRLNKT DTKPVQMMNM EATFCMGNID SINCKIIELP FQNKHLSMFI LLPKDVEDES
 241 TGLEKIEKQL NSESLSQWTN PSTMANAKVK LSIPKFKVEK MIDPKACLEN LGLKHIFSED
 301 TSDFSGMSET KGVALSNVIH KVCLEITEDG GDSIEVPGAR ILQHKDELNA DHPFIYIIRH
 361 NKTRNIIFFG KFCSP
```

FIG. 18

```
-956 AGATAAGCACAGCAGAGAAGCAACCAGCTCCGTTTCAGGTCCTTTCCTGAGGCTGATTCG -897
-896 GCTGGAAGGGAGTAGGTCCCACCAAATGAAGAAGCTGTGGGAAGACAGGAGGACAAGAAC -837
-836 AGGCTCCACGAAGAGATTTCAGAGCAGAGCTGCGTACTCCTTTTTCTTTTTGTTTCTTTT -777
-776 GCTCTGTCACCCAGGCTGAAGTACAGTGGTTAGCTCACGGCTCACTGCAGCTTTGACCTC -717
-716 CCAGGCTCAAGTGATCCTCTCGTCTCAGCTTTCCAAGTAACTGGGACCACAGGCATGCAT -657
-656 CACCACGCTAGGCTATTGTTTTACATTTTTTGTAGAGATGGGGTCTCACCATGTTGCCCA -597
-596 GGTTGGTCTCAAACTCCTGGGCTCAAGCAATCCGCTCACGTCAACCTCCCCAAATGCTGG -537
                                        AP2        AP1
-536 GATTACAGGCGTGAGCCACCG[GCCAGGG][TGAGTAA]TCCTAATCACAGGATTTTAAAAA -477
          Ets
-476 GAAA[CTTCCT]CGCCACCCATTAAACAATATCTCCTACCAATTTGGTAGTAAATATTTTG -417
-416 CTAATAGTACCTAATTTTTAGGTAGGCACTGTGTTTATACATATATCCATTCCTTCTTTT -357
-356 TTGATTGTCTTTCTGTTTAATGGGCAGCTACCTCTCTTGGCATCTAGCAGAATGAGCTGC -297
                              GRE
-296 TGCAGTTTACACAAAAAGAATGG[AGATCAGA]GTACTTTTTGTGCCACCAACGTGTCTGAG -237
-236 AAATTTGTAGTGTTACTATCATCACACATTACTTTTATTTCATCGAATATTTCACCTTCC -177
-176 GGTCCTGCGTGGGCCGAGAGGATTGCCGTACGCATGTCTGTACGTATGCATGTAACTCAC -117
         Ets
-116 AGCCC[CTTCCT]GCCCGAACATGTTGGAGGCCTTTTGGAAGCTGTGCAGACAACAGCAACT -57
          AP1
-56 TCAGCC[TGAATCA]TCTCTTTCAATTGTGGACAAGCTGCCAAGAGGCTTGAGTAGGAG
  1 AGGAGTGCCGCCGAGGCGGGGCGGGGCGGGGCGTGGAGCTGGGCTGGCAGTGGGCGTGGC  60
 61 GGTGCTGCCCAGGTGAGCCACCGCTGCTTCTGCCCAGACACGGTCGCCTCCACATCCAGG 120
121 TCTTTGTGCTCCTCGCTTGCCTGTTCCTTTTCCACGCATTTTCCAGGATAACTGTGACTC 180
181 CAGG
```

FIG. 19

The list of metastasis-related genes
a1: Beta-catenin
a2: BRMS1 (breast cancer metastasis suppressor-1)
a3: Cadherin
a4: Caspase 8
b1: CD44
b2: C-myc
b3: CRMP-1 (collapsin response mediator 1)
b4: CRSP3 (cofactor required for Sp1 transcriptional activation, subunit 3)
c1: Has1 (hyaluronan synthase1)
c2: Has2 (hyaluronan synthase2)
c3: Has3 (hyaluronan synthase3)
c4: HMG-1 (The high-mobility group protein 1)
d1: Hyal1 (Hyaluronoglucosaminidase 1)
d2: Hyal2 (Hyaluronoglucosaminidase 2)
d3: Hyal3 (Hyaluronoglucosaminidase 3)
d4: Hyal4 (Hyaluronoglucosaminidase 4)
e1: Hyal5 (Hyaluronoglucosaminidase 5)
e2: Integrin beta4
e3: Integrin-beta-1 e4: Gelsolin (Gsn)
f1: KAI1/CD82 (CD82 antigen)
f2: KISS1 (KiSS-1 metastasis-suppressor)
f3: LKB1 [serine/threonine kinase 11 (Stk11)]
f4: MKK4 (mitogen-activated protein kinase kinase 4)
g1: Maspin (also named SERPINB5, mammary homologue to serpins)
g2: MMP-2 (matrix metalloproteinase 2)
g3: MMP-3 (matrix metalloproteinase 3)
g4: MMP-7 (matrix metalloproteinase 7)
h1: MMP-9 (matrix metalloproteinase 9)
h2: MMP-14 (matrix metalloproteinase 14)
h3: Myo18B (myosin XVIIIb)
h4: NM23-1 [Nucleoside diphosphate kinases-1 (NDP kinases-1)]
i1: NM23-2 [Nucleoside diphosphate kinases-2 (NDP kinases-2)]
i2: NM23-3 [Nucleoside diphosphate kinases-3 (NDP kinases-3)]
i3: P16 i4: P19
j1: P21
j2: P27
j3: p63 [transformation related protein 63 (Trp63)]
j4: pten (Phosphatase and tensin homologue deleted on chromosome 10)
k1: RECK (reversion-inducing-cysteine-rich protein with Kazal motifs)
k2: RKIP-V1 (Raf-1 kinase inhibitor protein 1)
k3: RKIP-V2 (Raf-1 kinase inhibitor protein 2)
k4: SSeCKS (Src Suppressed C Kinase Substrate)
l1: Syntenin (also named Melanoma differentiation associated gene-9, mda-9)
l2: TIMP1 (tissue inhibitor 1 of metalloproteinases)
l3: TIMP2 (tissue inhibitor 2 of metalloproteinases)
l4: TIMP3 (tissue inhibitor 3 of metalloproteinases)
m1: TIMP4 (tissue inhibitor 4 of metalloproteinases)
m2: TSC1 (tuberous sclerosis 1)
m3: TSC2 (tuberous sclerosis 2)
m4: VDUP1 (thioredoxin interacting factor)

SEQUENCE LISTING

<160> NUMBER OF SEQ ID NOS: 11

<210> SEQ ID NO 1
<211> LENGTH: 19
<212> TYPE: DNA
<213> ORGANISM: Homo sapiens

```
<400> SEQUENCE: 1
gcagaatgag ctgctgcag                                              19

<210> SEQ ID NO 2
<211> LENGTH: 20
<212> TYPE: DNA
<213> ORGANISM: Homo sapiens

<400> SEQUENCE: 2
agaagcagcg gtggctcacc                                             20

<210> SEQ ID NO 3
<211> LENGTH: 20
<212> TYPE: DNA
<213> ORGANISM: Homo sapiens

<400> SEQUENCE: 3
aggagccagt cagcatagga                                             20

<210> SEQ ID NO 4
<211> LENGTH: 20
<212> TYPE: DNA
<213> ORGANISM: Homo sapiens

<400> SEQUENCE: 4
tttggctgca aacacctaca                                             20

<210> SEQ ID NO 5
<211> LENGTH: 29
<212> TYPE: DNA
<213> ORGANISM: Artificial sequence
<220> FEATURE:
<223> OTHER INFORMATION: Synthetic

<400> SEQUENCE: 5
gagactcgag gctgaagtac agtggttag                                   29

<210> SEQ ID NO 6
<211> LENGTH: 30
<212> TYPE: DNA
<213> ORGANISM: Artificial sequence
<220> FEATURE:
<223> OTHER INFORMATION: Synthetic

<400> SEQUENCE: 6
gagaaagctt agaagcagcg gtggctcacc                                  30

<210> SEQ ID NO 7
<211> LENGTH: 2273
<212> TYPE: DNA
<213> ORGANISM: Homo sapiens

<400> SEQUENCE: 7
tcgacggaac ctgaggccgc ttgccctccc gccccatgga gcggcccccg gggctgcggc     60
cgggcgcggg cgggccctgg gagatgcggg agcggctggg caccggcggc ttcgggaacg    120
tctgtctgta ccagcatcgg gaacttgatc tcaaaatagc aattaagtct tgtcgcctag    180
agctaagtac caaaaacaga gaacgatggt gccatgaaat ccagattatg aagaagttga    240
accatgccaa tgttgtaaag gcctgtgatg ttcctgaaga attgaatatt ttgattcatg    300
atgtgcctct tctagcaatg gaatactgtt ctggaggaga tctccgaaag ctgctcaaca    360
```

-continued

```
aaccagaaaa ttgttgtgga cttaaagaaa gccagatact ttctttacta agtgatatag    420
ggtctgggat tcgatatttg catgaaaaca aaattataca tcgagatcta aaacctgaaa    480
acatagttct tcaggatgtt ggtggaaaga taatacataa aataattgat ctgggatatg    540
ccaaagatgt tgatcaagga agtctgtgta catcttttgt gggaacactg cagtatctgg    600
ccccagagct cttttgagaat aagccttaca cagccactgt tgattattgg agctttggga   660
ccatggtatt tgaatgtatt gctggatata ggcctttttt gcatcatctg cagccattta    720
cctggcatga aagattaag aagaaggatc caaagtgtat atttgcatgt gaagagatgt     780
caggagaagt tcggtttagt agccatttac ctcaaccaaa tagcctttgt agtttaatag    840
tagaacccat ggaaaactgg ctacagttga tgttgaattg ggaccctcag cagagaggag    900
gacctgttga ccttactttg aagcagccaa gatgttttgt attaatggat cacatttga    960
atttgaagat agtacacatc ctaaatatga cttctgcaaa gataatttct tttctgttac    1020
cacctgatga aagtcttcat tcactacagt ctcgtattga gcgtgaaact ggaataaata   1080
ctggttctca agaacttctt tcagagacag gaatttctct ggatcctcgg aaaccagcct    1140
ctcaatgtgt tctagatgga gttagaggct gtgatagcta tggttttat ttgtttgata    1200
aaagtaaaac tgtatatgaa gggccatttg cttccagaag tttatctgat tgtgtaaatt    1260
atattgtaca ggacagcaaa atacagcttc aattataca gctgcgtaaa gtgtgggctg    1320
aagcagtgca ctatgtgtct ggactaaaag aagactatag caggctcttt cagggacaaa   1380
gggcagcaat gttaagtctt cttagatata atgctaactt aacaaaaatg aagaacactt   1440
tgatctcagc atcacaacaa ctgaaagcta aattggagtt ttttcacaaa agcattcagc   1500
ttgacttgga gagatacagc gagcagatga cgtatgggat atcttcagaa aaaatgctaa    1560
aagcatggaa agaaatggaa gaaaaggcca tccactatgc tgaggttggt gtcattggat    1620
acctggagga tcagattatg tctttgcatg ctgaaatcat ggggctacag aagagcccct    1680
atggaagacg tcagggagac ttgatggaat ctctggaaca gcgtgccatt gatctatata    1740
agcagttaaa acacagacct tcagatcact cctacagtga cagcacagag atggtgaaaa    1800
tcattgtgca cactgtgcag agtcaggacc gtgtgctcaa ggagctgttt ggtcatttga    1860
gcaagttgtt gggctgtaag cagaagatta ttgatctact ccctaaggtg gaagtggccc    1920
tcagtaatat caaagaagct gacaatactg tcatgttcat gcagggaaaa aggcagaaag    1980
aaatatggca tctccttaaa attgcctgta cacagagttc tgcccgctct cttgtaggat    2040
ccagtctaga aggtgcagta acccctcaga catcagcatg gctgccccg acttcagcag    2100
aacatgatca ttctctgtca tgtgtggtaa ctcctcaaga tggggagact tcagcacaaa    2160
tgatagaaga aaatttgaac tgccttggcc atttaagcac tattattcat gaggcaaatg    2220
aggaacaggg caatagtatg atgaatcttg attggagttg gttaacagaa tga           2273
```

<210> SEQ ID NO 8
<211> LENGTH: 745
<212> TYPE: PRT
<213> ORGANISM: Homo sapiens

<400> SEQUENCE: 8

```
Met Glu Arg Pro Pro Gly Leu Arg Pro Gly Ala Gly Gly Pro Trp Glu
1               5                   10                  15

Met Arg Glu Arg Leu Gly Thr Gly Gly Phe Gly Asn Val Cys Leu Tyr
            20                  25                  30
```

-continued

```
Gln His Arg Glu Leu Asp Leu Lys Ile Ala Ile Lys Ser Cys Arg Leu
         35                  40                  45

Glu Leu Ser Thr Lys Asn Arg Glu Arg Trp Cys His Glu Ile Gln Ile
 50                  55                  60

Met Lys Lys Leu Asn His Ala Asn Val Val Lys Ala Cys Asp Val Pro
 65                  70                  75                  80

Glu Glu Leu Asn Ile Leu Ile His Asp Val Pro Leu Leu Ala Met Glu
                 85                  90                  95

Tyr Cys Ser Gly Gly Asp Leu Arg Lys Leu Leu Asn Lys Pro Glu Asn
                100                 105                 110

Cys Cys Gly Leu Lys Glu Ser Gln Ile Leu Ser Leu Leu Ser Asp Ile
            115                 120                 125

Gly Ser Gly Ile Arg Tyr Leu His Glu Asn Lys Ile Ile His Arg Asp
130                 135                 140

Leu Lys Pro Glu Asn Ile Val Leu Gln Asp Val Gly Gly Lys Ile Ile
145                 150                 155                 160

His Lys Ile Ile Asp Leu Gly Tyr Ala Lys Asp Val Asp Gln Gly Ser
                165                 170                 175

Leu Cys Thr Ser Phe Val Gly Thr Leu Gln Tyr Leu Ala Pro Glu Leu
            180                 185                 190

Phe Glu Asn Lys Pro Tyr Thr Ala Thr Val Asp Tyr Trp Ser Phe Gly
        195                 200                 205

Thr Met Val Phe Glu Cys Ile Ala Gly Tyr Arg Pro Phe Leu His His
210                 215                 220

Leu Gln Pro Phe Thr Trp His Glu Lys Ile Lys Lys Asp Pro Lys
225                 230                 235                 240

Cys Ile Phe Ala Cys Glu Glu Met Ser Gly Glu Val Arg Phe Ser Ser
                245                 250                 255

His Leu Pro Gln Pro Asn Ser Leu Cys Ser Leu Ile Val Glu Pro Met
            260                 265                 270

Glu Asn Trp Leu Gln Leu Met Leu Asn Trp Asp Pro Gln Gln Arg Gly
        275                 280                 285

Gly Pro Val Asp Leu Thr Leu Lys Gln Pro Arg Cys Phe Val Leu Met
290                 295                 300

Asp His Ile Leu Asn Leu Lys Ile Val His Ile Leu Asn Met Thr Ser
305                 310                 315                 320

Ala Lys Ile Ile Ser Phe Leu Leu Pro Pro Asp Glu Ser Leu His Ser
                325                 330                 335

Leu Gln Ser Arg Ile Glu Arg Glu Thr Gly Ile Asn Thr Gly Ser Gln
            340                 345                 350

Glu Leu Leu Ser Glu Thr Gly Ile Ser Leu Asp Pro Arg Lys Pro Ala
        355                 360                 365

Ser Gln Cys Val Leu Asp Gly Val Arg Gly Cys Asp Ser Tyr Met Val
370                 375                 380

Tyr Leu Phe Asp Lys Ser Lys Thr Val Tyr Glu Gly Pro Phe Ala Ser
385                 390                 395                 400

Arg Ser Leu Ser Asp Cys Val Asn Tyr Ile Val Gln Asp Ser Lys Ile
                405                 410                 415

Gln Leu Pro Ile Ile Gln Leu Arg Lys Val Trp Ala Glu Ala Val His
            420                 425                 430

Tyr Val Ser Gly Leu Lys Glu Asp Tyr Ser Arg Leu Phe Gln Gly Gln
        435                 440                 445
```

-continued

```
Arg Ala Ala Met Leu Ser Leu Leu Arg Tyr Asn Ala Asn Leu Thr Lys
    450                 455                 460

Met Lys Asn Thr Leu Ile Ser Ala Ser Gln Gln Leu Lys Ala Lys Leu
465                 470                 475                 480

Glu Phe Phe His Lys Ser Ile Gln Leu Asp Leu Glu Arg Tyr Ser Glu
                485                 490                 495

Gln Met Thr Tyr Gly Ile Ser Ser Glu Lys Met Leu Lys Ala Trp Lys
            500                 505                 510

Glu Met Glu Glu Lys Ala Ile His Tyr Ala Glu Val Gly Val Ile Gly
        515                 520                 525

Tyr Leu Glu Asp Gln Ile Met Ser Leu His Ala Glu Ile Met Gly Leu
    530                 535                 540

Gln Lys Ser Pro Tyr Gly Arg Arg Gln Gly Asp Leu Met Glu Ser Leu
545                 550                 555                 560

Glu Gln Arg Ala Ile Asp Leu Tyr Lys Gln Leu Lys His Arg Pro Ser
                565                 570                 575

Asp His Ser Tyr Ser Asp Ser Thr Glu Met Val Lys Ile Ile Val His
            580                 585                 590

Thr Val Gln Ser Gln Asp Arg Val Leu Lys Glu Leu Phe Gly His Leu
        595                 600                 605

Ser Lys Leu Leu Gly Cys Lys Gln Lys Ile Ile Asp Leu Leu Pro Lys
    610                 615                 620

Val Glu Val Ala Leu Ser Asn Ile Lys Glu Ala Asp Asn Thr Val Met
625                 630                 635                 640

Phe Met Gln Gly Lys Arg Gln Lys Glu Ile Trp His Leu Leu Lys Ile
                645                 650                 655

Ala Cys Thr Gln Ser Ser Ala Arg Ser Leu Val Gly Ser Ser Leu Glu
            660                 665                 670

Gly Ala Val Thr Pro Gln Thr Ser Ala Trp Leu Pro Pro Thr Ser Ala
        675                 680                 685

Glu His Asp His Ser Leu Ser Cys Val Val Thr Pro Gln Asp Gly Glu
    690                 695                 700

Thr Ser Ala Gln Met Ile Glu Glu Asn Leu Asn Cys Leu Gly His Leu
705                 710                 715                 720

Ser Thr Ile Ile His Glu Ala Asn Glu Glu Gln Gly Asn Ser Met Met
                725                 730                 735

Asn Leu Asp Trp Ser Trp Leu Thr Glu
            740                 745
```

<210> SEQ ID NO 9
<211> LENGTH: 1128
<212> TYPE: DNA
<213> ORGANISM: Homo sapiens

<400> SEQUENCE: 9

```
atggatgccc tgcaactagc aaattcggct tttgccgttg atctgttcaa acaactatgt      60
gaaaaggagc cactgggcaa tgtcctcttc tctccaatct gtctctccac ctctctgtca     120
cttgctcaag tgggtgctaa aggtgacact gcaaatgaaa ttggacaggt tcttcatttt     180
gaaaatgtca agatatacc ctttggattt caaacagtaa catcggatgt aaacaaactt     240
agttcctttt actcactgaa actaatcaag cggctctacg tagacaaatc tctgaatctt     300
tctacagagt tcatcagctc tacgaagaga ccctatgcaa aggaattgga aactgttgac     360
ttcaaagata aattggaaga aacgaaaggt cagatcaaca actcaattaa ggatctcaca     420
```

```
gatggccact tgagaacat ttagctgac aacagtgtga acgaccagac caaaatcctt    480
gtggttaatg ctgcctactt tgttggcaag tggatgaaga atttcctga atcagaaaca    540 aaagaatgtc ctttcagact caacaagaca gacaccaaac cagtgcagat gatgaacatg    600
gaggccacgt tctgtatggg aaacattgac agtatcaatt gtaagatcat agagcttcct    660
tttcaaaata gcatctcag catgttcatc ctactaccca aggatgtgga ggatgagtcc    720
acaggcttgg agaagattga aaacaactc aactcagagt cactgtcaca gtggactaat    780
cccagcacca tggccaatgc caaggtcaaa ctctccattc aaaatttaa ggtggaaaag    840 atgattgatc ccaaggcttg tctggaaaat ctagggctga acatatctt cagtgaagac    900 acatctgatt tctctggaat gtcagagacc aagggagtgg ccctatcaaa tgttatccac    960
aaagtgtgct tagaaataac tgaagatggt ggggattcca tagaggtgcc aggagcacgg    1020
atcctgcagc acaaggatga attgaatgct gaccatccct ttatttacat catcaggcac    1080
aacaaaactc gaaacatcat tttctttggc aaattctgtt ctccttaa                 1128
```

<210> SEQ ID NO 10
<211> LENGTH: 375
<212> TYPE: PRT
<213> ORGANISM: Homo sapiens

<400> SEQUENCE: 10

```
Met Asp Ala Leu Gln Leu Ala Asn Ser Ala Phe Ala Val Asp Leu Phe
1               5                   10                  15

Lys Gln Leu Cys Glu Lys Glu Pro Leu Gly Asn Val Leu Phe Ser Pro
            20                  25                  30

Ile Cys Leu Ser Thr Ser Leu Ser Leu Ala Gln Val Gly Ala Lys Gly
        35                  40                  45

Asp Thr Ala Asn Glu Ile Gly Gln Val Leu His Phe Glu Asn Val Lys
    50                  55                  60

Asp Ile Pro Phe Gly Phe Gln Thr Val Thr Ser Asp Val Asn Lys Leu
65                  70                  75                  80

Ser Ser Phe Tyr Ser Leu Lys Leu Ile Lys Arg Leu Tyr Val Asp Lys
                85                  90                  95

Ser Leu Asn Leu Ser Thr Glu Phe Ile Ser Ser Thr Lys Arg Pro Tyr
            100                 105                 110

Ala Lys Glu Leu Glu Thr Val Asp Phe Lys Asp Lys Leu Glu Glu Thr
        115                 120                 125

Lys Gly Gln Ile Asn Asn Ser Ile Lys Asp Leu Thr Asp Gly His Phe
    130                 135                 140

Glu Asn Ile Leu Ala Asp Asn Ser Val Asn Asp Gln Thr Lys Ile Leu
145                 150                 155                 160

Val Val Asn Ala Ala Tyr Phe Val Gly Lys Trp Met Lys Lys Phe Pro
                165                 170                 175

Glu Ser Glu Thr Lys Glu Cys Pro Phe Arg Leu Asn Lys Thr Asp Thr
            180                 185                 190

Lys Pro Val Gln Met Met Asn Met Glu Ala Thr Phe Cys Met Gly Asn
        195                 200                 205

Ile Asp Ser Ile Asn Cys Lys Ile Ile Glu Leu Pro Phe Gln Asn Lys
    210                 215                 220

His Leu Ser Met Phe Ile Leu Leu Pro Lys Asp Val Glu Asp Glu Ser
225                 230                 235                 240

Thr Gly Leu Glu Lys Ile Glu Lys Gln Leu Asn Ser Glu Ser Leu Ser
                245                 250                 255
```

```
Gln Trp Thr Asn Pro Ser Thr Met Ala Asn Ala Lys Val Lys Leu Ser
                260                 265                 270

Ile Pro Lys Phe Lys Val Glu Lys Met Ile Asp Pro Lys Ala Cys Leu
            275                 280                 285

Glu Asn Leu Gly Leu Lys His Ile Phe Ser Glu Asp Thr Ser Asp Phe
        290                 295                 300

Ser Gly Met Ser Glu Thr Lys Gly Val Ala Leu Ser Asn Val Ile His
305                 310                 315                 320

Lys Val Cys Leu Glu Ile Thr Glu Asp Gly Gly Asp Ser Ile Glu Val
                325                 330                 335

Pro Gly Ala Arg Ile Leu Gln His Lys Asp Glu Leu Asn Ala Asp His
                340                 345                 350

Pro Phe Ile Tyr Ile Ile Arg His Asn Lys Thr Arg Asn Ile Ile Phe
            355                 360                 365

Phe Gly Lys Phe Cys Ser Pro
        370                 375

<210> SEQ ID NO 11
<211> LENGTH: 1141
<212> TYPE: DNA
<213> ORGANISM: Homo sapiens

<400> SEQUENCE: 11
agataagcac agcagagaag caaccagctc cgtttcaggt cctttcctga ggctgattcg      60
gctggaaggg agtaggtccc accaaatgaa gaagctgtgg gaagacagga ggacaagaac     120
aggctccacg aagagatttc agagcagagc tgcgtactcc tttttctttt tgtttctttt     180
gctctgtcac ccaggctgaa gtacagtggt tagctcacgg ctcactgcag ctttgacctc     240
ccaggctcaa gtgatcctct cgtctcagct ttccaagtaa ctgggaccac aggcatgcat     300
caccacgcta ggctattgtt ttacattttt tgtagagatg gggtctcacc atgttgccca     360
ggttggtctc aaactcctgg gctcaagcaa tccgctcacg tcaacctccc aaatgctgg      420
gattacaggc gtgagccacc gcgccaggcc tgagtaatcc taatcacagg attttaaaaa     480
gaaacttcct gcgccaccca ttaaacaata tctcctacca atttggtagt aaatattttg     540
ctaatagtac ctaatttta ggtaggcact gtgtttatac atatatccat tccttctttt      600
ttgattgtct ttctgtttaa tgggcagcta cctctcttgg catctagcag aatgagctgc     660
tgcagtttac acaaaaagaa tggagatcag agtactttt gtgccaccaa cgtgtctgag      720
aaatttgtag tgttactatc atcacacatt acttttattt catcgaatat ttcaccttcc     780
ggtcctgcgt gggccgagag gattgccgta cgcatgtctg tacgtatgca tgtaactcac     840
agccccttcc tgcccgaaca tgttggaggc cttttggaag ctgtgcagac aacagcaact     900
tcagcctgaa tcatctcttt caattgtgga caagctgcca agaggcttga gtaggagagg     960
agtgccgccg aggcggggcg gggcggggcg tggagctggg ctggcagtgg gcgtggcggt    1020
gctgcccagg tgagccaccg ctgcttctgc ccagacacgg tcgcctccac atccaggtct    1080
ttgtgctcct cgcttgcctg ttccttttcc acgcattttc caggataact gtgactccag    1140
g                                                                    1141
```

METHOD FOR DETECTING THE PRESENCE OF PROSTATE CANCER

This application claims the benefit of U.S. Provisional Application Ser. No. 60/876,743, filed on Dec. 21, 2006.

This invention was made in part with Government support from Grant No. DE-FG03-86ER60429, awarded by the Department of Energy. As such the United States Government has certain rights in this invention.

FIELD OF THE INVENTION

The present invention relates to compositions and methods for cancer diagnosis, treatment and drug screening. In particular, the present invention provides compositions and methods for targeting the nuclear translocation of IkB kinase-α (IKKα) and the IKKα-mediated suppression of maspin expression observed in metastatic prostate cancer cells.

BACKGROUND OF THE INVENTION

Prostate cancer is a heterogeneous disease progressing from prostatic intraepithelial neoplasia via locally invasive adenocarcinoma to hormone-refractory metastatic carcinoma (Demarzo et al., Lancet, 361:955, 2003). Prostate cancer develops most frequently in men over fifty, with more than 200,000 new cases diagnosed annually in the United States. Currently the second leading cause of cancer death in men is prostate cancer, exceeded only by lung cancer. It accounts for 29% of all male cancers and 11% of male cancer-related deaths.

Prostate cancer is typically diagnosed with a digital rectal exam and/or prostate specific antigen (PSA) screening (Schroder, Annal Oncol, 17(S10):201, 2006). An elevated serum PSA level is used as a marker for prostate cancer as only prostate cells secreted PSA. A healthy prostate will produce a stable amount, typically below 4 nanograms per milliliter, or a PSA level of 4 or less. Cancer cells on the other hand produce escalating amounts that correspond with the severity of the cancer. A level between 4 and 10 may raise a doctor's suspicion that a patient has prostate cancer, while amounts above 50 may show that the tumor has spread elsewhere in the body.

A major limitation of the serum PSA test is a lack of prostate cancer sensitivity and specificity especially in the intermediate range of PSA detection (4-10 ng/ml). Elevated serum PSA levels are often detected in patients with non-malignant conditions and provide little information about the aggressiveness of the cancer detected. Coincident with increased serum PSA testing, there has been a dramatic increase in the number of prostate needle biopsies performed (Jacobsen et al., JAMA, 274:1445, 1995), resulting in a surge of equivocal prostate needle biopsies (Epstein and Potter, J Urol, 166:402, 2001). Thus, development of additional serum and tissue biomarkers to supplement PSA screening is needed.

When initially diagnosed, prostate cancer in most patients is managed with either close observation in the absence of intervention (e.g., watchful waiting), surgical removal of the prostate (e.g., radical prostatectomy) or radiation involving the placement of radioactive pellets into the prostate (e.g., brachytherapy). However, for patients initially diagnosed with metastatic disease, it is already too late to perform brachytherapy or a radical prostatectomy. Therefore, these patients are typically treated initially with some type of testosterone suppressive therapy (Horwich, Annal Oncol, 17(S10):211, 2006). Once their cancer becomes hormone refractory, the median survival is 10-24 months.

Thus, additional methods that can be used for diagnosis and prognosis of prostate cancer are desirable. Moreover effective therapies for treating metastatic disease are needed. Accordingly, provided herein are methods that can be used in diagnosis and prognosis of prostate cancer. Further provided are methods that can be used to screen candidate bioactive agents for the ability to modulate signaling pathways in prostate cancer cells.

SUMMARY OF THE INVENTION

The present invention relates to compositions and methods for cancer diagnosis, treatment and drug screening. In particular, the present invention provides compositions and methods for targeting the nuclear translocation of IkB kinase-α (IKKα) and the IKKα-mediated suppression of maspin expression observed in metastatic prostate cancer cells.

Specifically, the present invention provides methods for characterizing a tumor cell sample of a subject, comprising: a) providing a tumor cell sample from a subject; and b) detecting the presence or absence of an increased level of nuclear IKKα in the tumor cell sample relative to the level of nuclear IKKα in a normal cell sample, thereby characterizing the tumor cell sample. In some embodiments the subject is a human patient. 2. In some embodiments, the tumor is a prostate tumor. In some preferred embodiments, the human patient has an intermediate (4-10) or high (greater than 10) level of serum prostate specific antigen. In some preferred embodiments, the nuclear IKKα is phosphorylated IKKα. Additionally, some methods further comprise detecting the presence or absence of a reduced level of Maspin (e.g., mRNA or protein) in the sample, relative to the level of Mapsin in the normal cell sample. In some embodiments, the characterizing the prostate tumor comprises identifying a stage of prostate cancer in the prostate tumor cell sample. In some preferred embodiments, the stage is selected from the group consisting of high-grade prostatic intraepithelial neoplasia, benign prostatic hyperplasia, prostate carcinoma, and metastatic prostate carcinoma. Some methods further comprise the step of c) providing a prognosis to the subject. In some preferred embodiments, the prognosis comprises a risk of developing metastatic prostate cancer, whereas in a subset of these embodiments, the prognosis comprises the risk of prostate cancer recurrence after prostatectomy. In some embodiments, the presence of an increased level of the nuclear IKKα in the sample is indicative of metastatic cancer in the subject. In additional embodiments, the methods further comprise step d) administering a metastasis regulating agent to the subject. In some embodiments, the metastasis-regulating agent is a compound that reduces nuclear IKKα accumulation in a metastatic prostate tumor cell sample.

The present invention also provides methods of screening a test compound, comprising: a) providing a cell comprising a constitutively active IKKα (IKKαEE), wherein said cell further comprises a maspin promoter in operable combination with a reporter; b) contacting the cell with a test compound to produce a treated cell; and c) measuring an increased level of expression of the reporter in the treated cell (relative to a control cell or an untreated cell). In some embodiments, the test compound is identified as a candidate anti-metastasis agent. In some preferred embodiments, the methods further comprise: d) providing an isolated IKKα; e) contacting the IKKα with the test compound; and f) detecting binding of the test compound to the IKKα. In preferred embodiments, the cell is a prostate tumor cell. In some preferred embodiments, the cell is a mammalian cell selected from but not limited to a human cell, a nonhuman primate cell and a rodent cell. In some preferred embodiments, the cell lacks a functional endogenous IKKα.

Additionally, the present invention provides methods of screening a test compound, comprising: a) providing a cell comprising nuclear IKKα; b) contacting the cell with a test compound to produce a treated cell; and c) detecting a reduction in nuclear IKKα. In some embodiments, the cell is a prostate tumor cell. In some preferred embodiments, the cell is a mammalian cell selected from but not limited to a human cell, a nonhuman primate cell and a rodent cell. In some preferred embodiments, the cell lacks a functional endogenous IKKα. In some embodiments, the test compound is identified as a candidate anti-metastasis agent. In some preferred embodiments, the methods further comprise: d) providing an isolated IKKα; e) contacting the IKKα with the test compound; and f) detecting binding of the test compound to the IKKα.

BRIEF DESCRIPTION OF THE DRAWINGS

FIG. 3A-E shows that Maspin expression correlates with the extent of metastasis. a, Expression of mRNAs encoding metastasis-suppressors was analyzed by RT-PCR in primary (P) CaPs and lymph node (L) metastases. b, c, Maspin expression was examined in primary CaPs of 4-5 months-old (b) or 7-8 months-old (c) WT/TRAMP and Ikkα$^{AA/AA}$/TRAMP mice by immunoblotting. d, e, Immunohistochemical staining for maspin in paraffin-embedded prostate carcinoma sections from Ikkα$^{AA/AA}$/TRAMP (d) and WT/TRAMP (e) mice. Numbers in b refer to different tumor isolates.

FIG. 5A-E shows that IKKα activation represses maspin transcription. a, Primary Ikkα$^{AA/AA}$/TRAMP CaP cells were infected with different adenoviruses as indicated. After 3 days, maspin, IKKα, IKKβ and actin levels were analyzed by immunoblotting. b, A maspin-luciferase reporter containing 759 base pairs (bp) of the human maspin 5' upstream region was co-transfected with different amounts of WT IKKα, IKKα(AA) or IKKα(EE) vectors into Ikkα$^{-/-}$ MEFs. Luciferase activity was measured and normalized to a co-transfected PRL-TK reporter. c, The maspin-luciferase reporter was co-transfected with IKKα(EE) or IKKβ(EE) vectors into Ikkα$^{-/-}$ MEFs. Luciferase activity was measured and normalized as above. d, Different maspin promoter truncation mutants fused to luciferase were co-transfected with or without IKKα(EE) expression vector as above and luciferase activity was measured. Results denote fold-repression by IKKα(EE) based on 3 separate experiments. e, ChIP analysis of IKKα recruitment to the human maspin promoter. HME cells were transduced with either HA-IKKα (EE) or GFP adenovirus. After 48 hrs proteins were crosslinked to DNA and chromatin was extracted and fragmented. Protein-DNA complexes were immunoprecipitated with HA antibody. Presence of the maspin promoter region (87 to −315) and intron 2 (+3958 to +4350) in the immunoprecipitates was examined by PCR.

FIG. 7A-E show that metastatic progression correlates with inflammatory cell infiltration and massive upregulation of RANKL, a negative regulator of maspin expression. a, Prostate tumors from 4-5 and 7-9 month-old TRAMP mice of the indicated genotype were stained for the T cell marker CD3. b, c, Prostate tumors from mice of the indicated age and genotype were analyzed by Q-PCR for expression of RANKL (b) and LTα (c) mRNAs. d, WT and Ikkα$^{AA/AA}$ prostate epithelial cells were cultured for 4-5 days and treated with LPS-free RANKL (200 μg/ml). At the indicated times cell extracts were prepared and examined for maspin and p38α content by immunoblotting. e, A model explaining how RANK signaling leads to repression of maspin transcription. After transient IKKα-mediated repression, maspin transcription is likely to be permanently silenced through DNA methylation.

Figure 8:
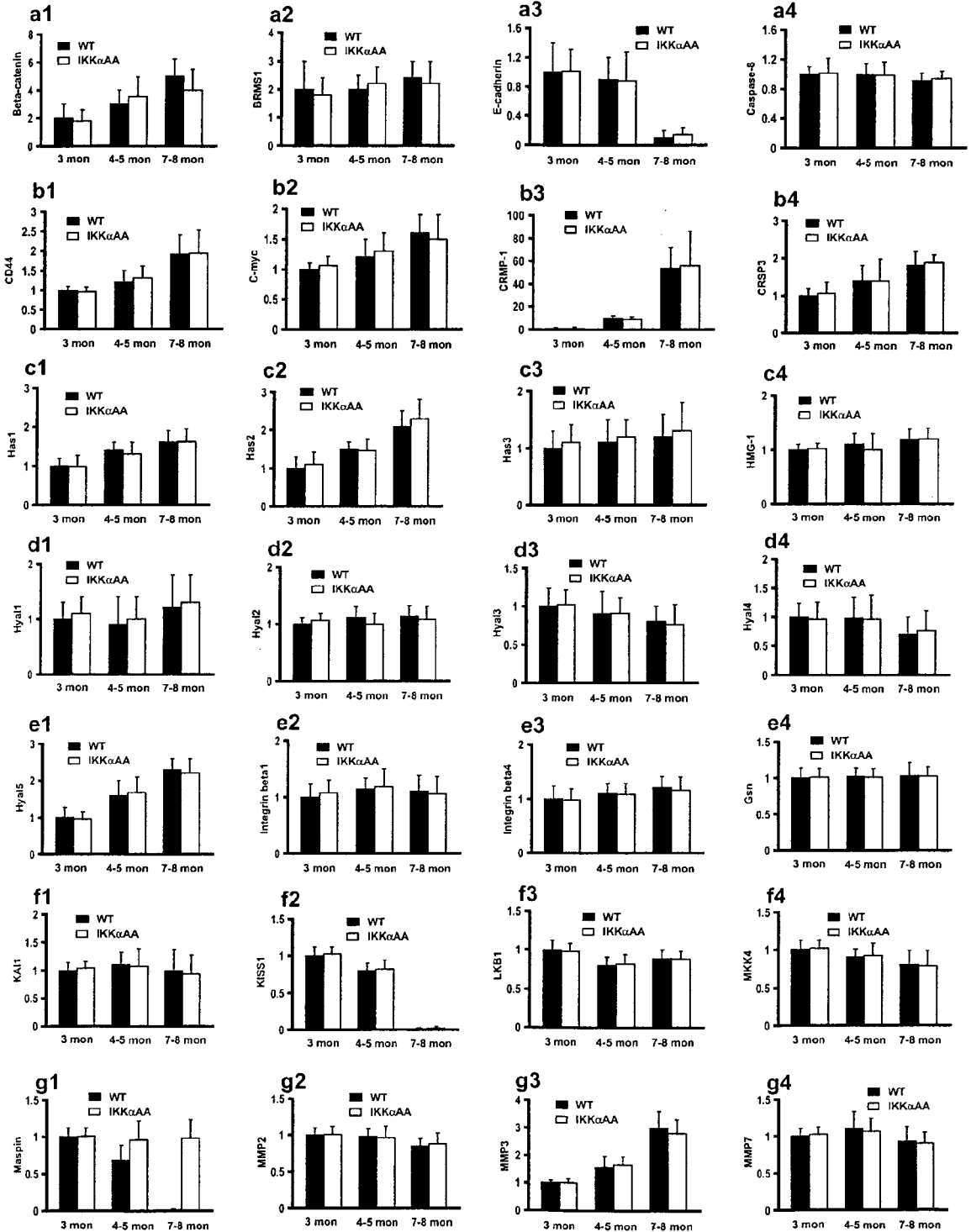
Figure 8:
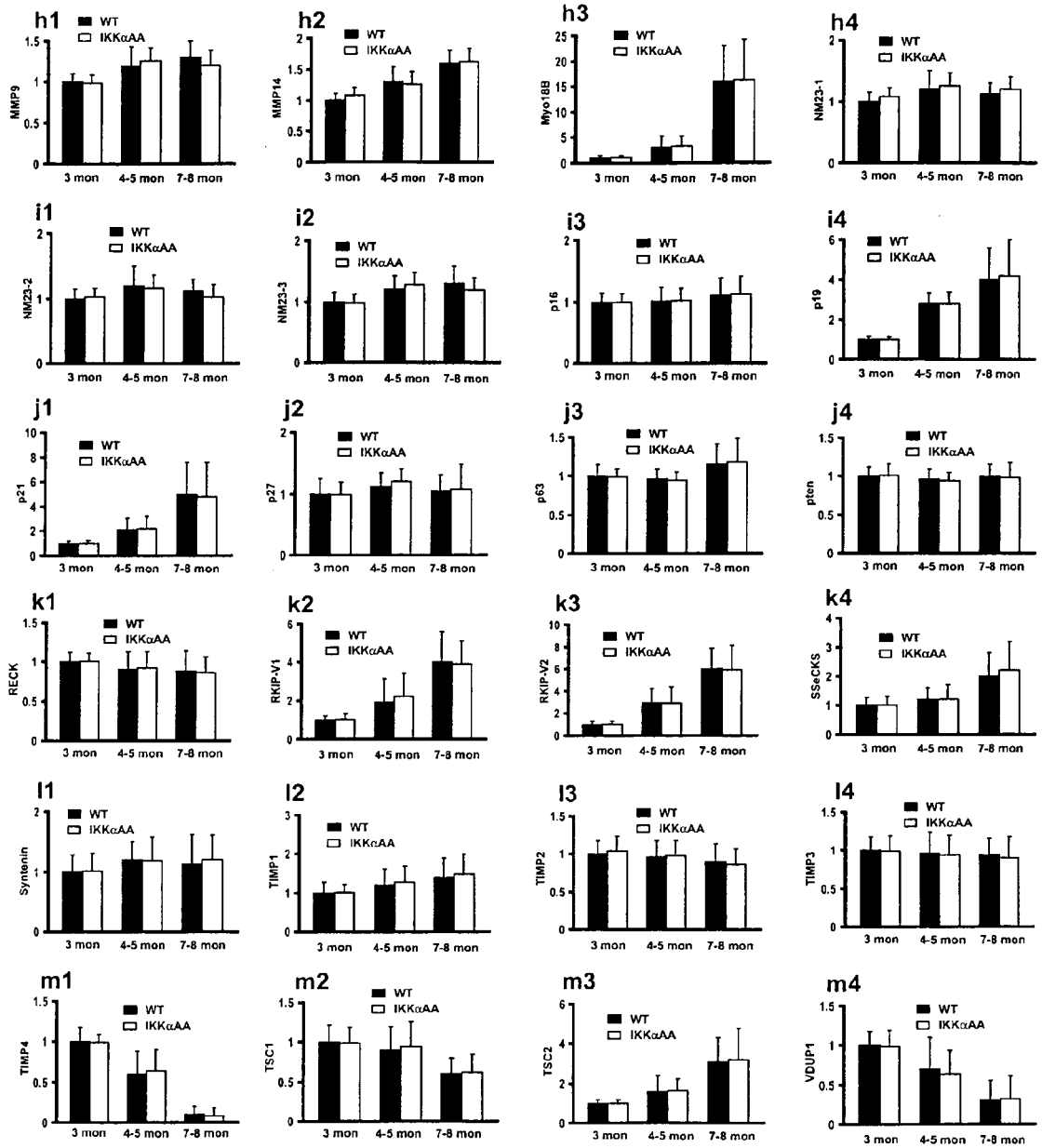

FIG. 8 a1-a4, b1-b4, c1-c4, d1-d4, e1-e4, f1-f4, g1-g4, h1-h4, i1-i4, j1-j4, k1-k4, l1-l4, and m1-m4 shows the expression of metastasis enhancers and suppressors. Expression of the indicated genes linked to either enhancement or repression of metastasis was examined by Q-PCR in prostates of WT/TRAMP and Ikkα$^{AA/AA}$/TRAMP mice at different ages and normalized to cyclophilin mRNA level.

Figure 9:
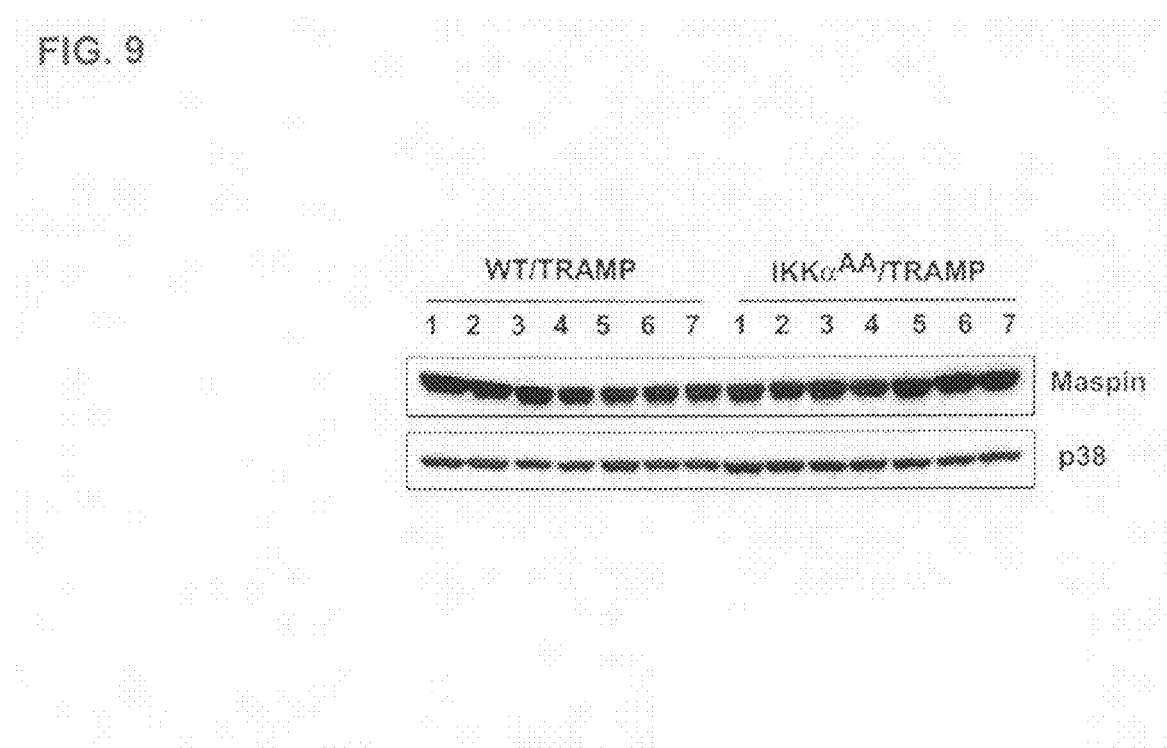

FIG. 9 shows Maspin and p38 protein expression in an immunoblot. Maspin protein expression in cancerous prostate tissues of 3 months-old Ikkα$^{AA/AA}$/TRAMP and WT/TRAMP mice was examined in relation to the p38 loading control. Numbers=individual mice.

Figure 10:
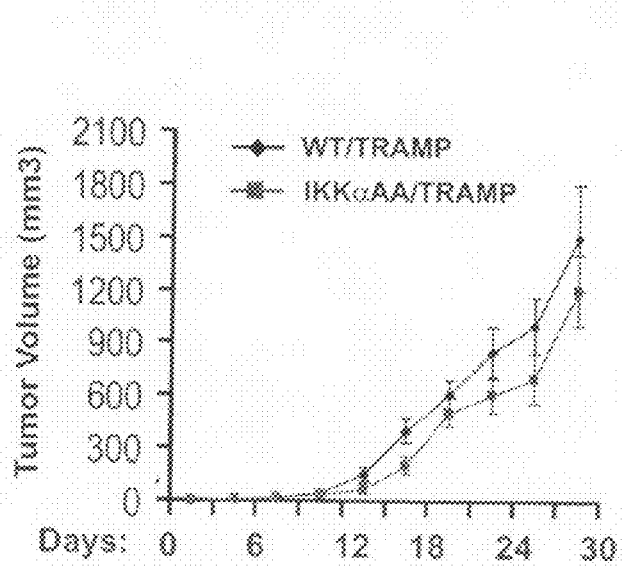

FIG. 10 shows that primary CaP cells from WT/TRAMP and Ikkα$^{AA/AA}$/TRAMP exhibit similar tumorigenic potential. Primary CaP cells (4×10$^6$) from 7-8 month-old WT/TRAMP and Ikkα$^{AA/AA}$/TRAMP mice were mixed in matrigel and implanted subcutaneously into the flank of male Nu/Nu mice. Tumor size was measured every three days using a caliper. Results are averages from three individual mice per CaP genotype.

FIG. 11A shows that equal numbers of WT/TRAMP CaP cells infected with either empty retrovirus or maspin-retrovirus (same cells as in FIG. 4C) were seeded at day 0 and cell number was determined every other day. b, Equal numbers of Ikkα$^{AA/AA}$/TRAMP CaP cells infected with empty retrovirus or maspin siRNA retrovirus (same cells as in FIG. 4F) were seeded at day 0 and cell number was determined every other day.

Figure 12:
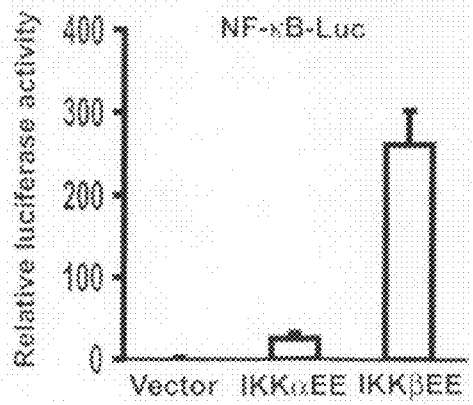

FIG. 12 shows NF-κB-luciferase reporter activity of Ikkα$^{-/-}$ MEFs cells co-transfected with IKKα(EE) or IKKβ(EE) expression vectors. Luciferase activity was measured after 36 hrs and normalized to that of a co-transfected internal control (purls-TK).

Figure 13:
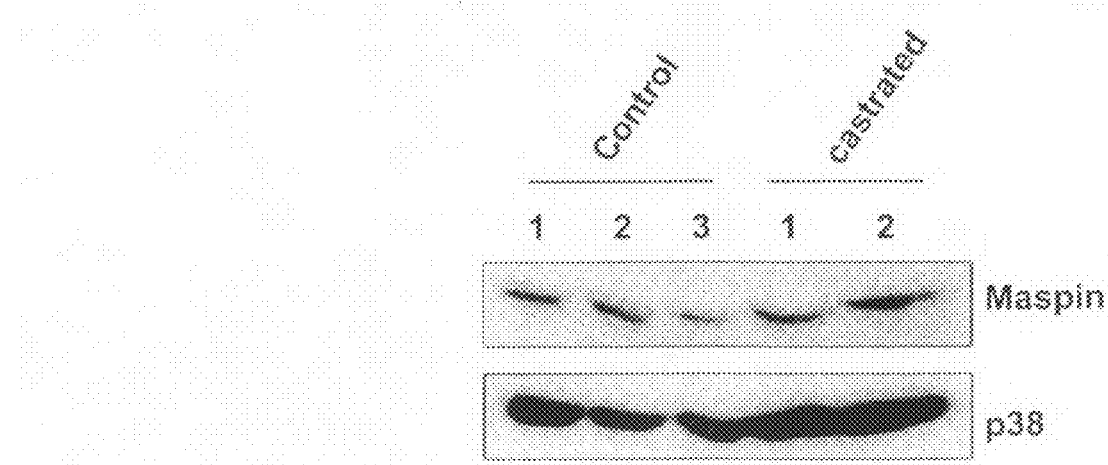

FIG. 13 shows Maspin and p38 protein expression in an immunoblot. Four-month old male mice were divided into two groups, one group was castrated and the other group was sham operated. One-week later mice were sacrificed and prostate tissues were collected and lysed for analysis.

FIG. 14 shows that IKKα represses maspin transcription independency of androgen receptor (AR). a, Human maspin-luciferase reporter (pM-759-Luc) was co-transfected with empty, IKKα(EE), AR, or IKKα(EE)+AR expression vectors into Ikkα$^{-/-}$ MEFs. Luciferase activity was measured and normalized as above. b, pM-759-Luc was co-transfected with vector+AR, or IKKα(EE)+AR into Ikkα$^{-/-}$ MEFs. After 36 hrs the cells were incubated with dihydrotestosterone (DHT) and luciferase activity was determined and normalized as above. c, pM-759-Luc or ARE-mutant-pM-Luc was co-transfected with empty vector or IKKα(EE) into Ikkα$^{-/-}$ MEFs. Luciferase activity was measured and normalized as above.

Figure 15:
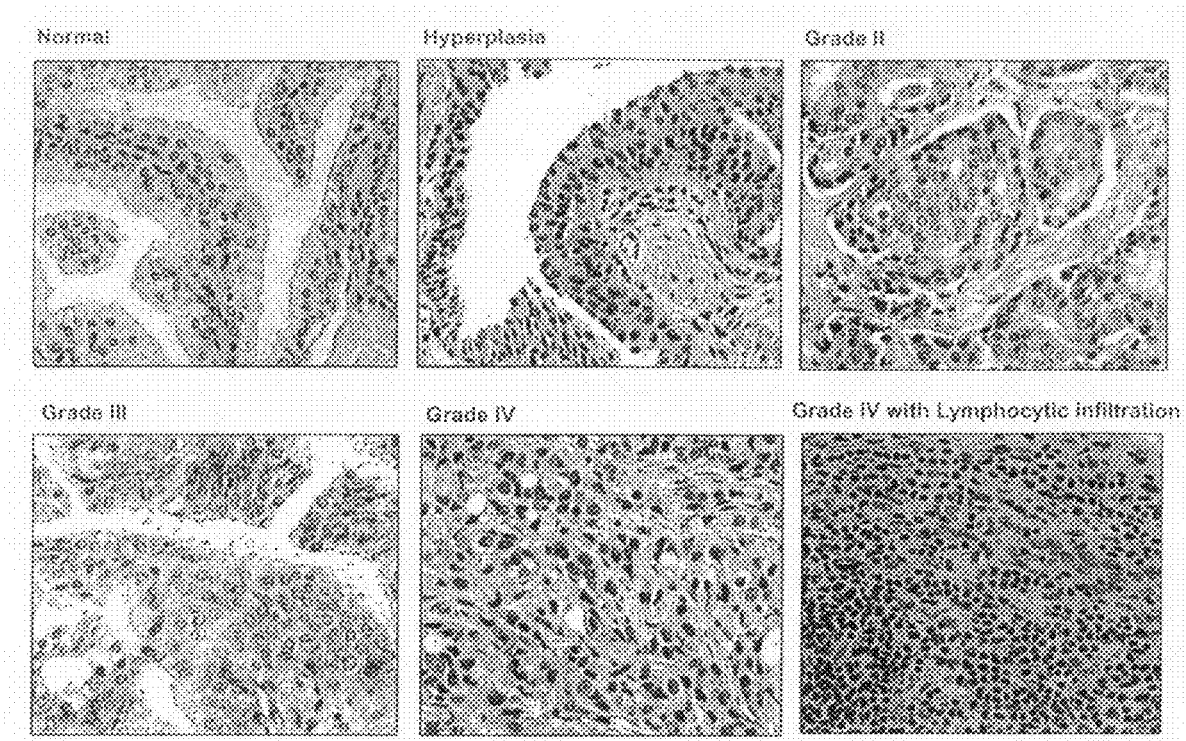

FIG. 15 provides images of a histological examination of human prostate tissues. Frozen sections of normal prostate, prostatic hyperplasia and prostate cancer at different stages of progression were H&E stained and examined by light microscopy (magnification 200×).

FIG. 16A-B provides cDNA (SEQ ID NO:7) and protein (SEQ ID NO:8) sequences for human IKKα. The coding region of IKKα extends from residues 36 to 2273 of SEQ ID NO:7.

FIG. 17A-B provides cDNA (SEQ ID NO:9) and protein (SEQ ID NO: 10) sequences for human maspin.

FIG. 18 provides a sequence comprising the promoter and a partial cDNA of human maspin (SEQ ID NO:1 1). The major transcription start site is numbered 1. The putative transcription factor binding sites are boxed.

FIG. 19 provides a listing of metastasis-related genes examined in FIG. 8.

DEFINITIONS

To facilitate an understanding of the present invention, a number of terms and phrases are defined below:

The terms "mammals" and "mammalian" refer animals of the class mammalia, which nourish their young by fluid secreted from mammary glands of the mother, including but not limited to, humans, nonhuman primates, rodents, and the like. The class "mammalian" includes placental animals, marsupial animals, and monotrematal animals.

As used herein, the term "non-human animals" refers to all non-human animals including, but are not limited to, vertebrates such as rodents, non-human primates, ovines, bovines, ruminants, lagomorphs, porcines, caprines, equines, canines, felines, aves, etc.

The terms "patient" and "subject" refer to a human or other mammal that is a candidate for receiving medical treatment.

As used herein, the term "subject suspected of having cancer" refers to a subject that presents one or more symptoms indicative of a cancer (e.g., a noticeable lump or mass) or is being screened for a cancer (e.g., during a routine physical). A subject suspected of having cancer may also have one or more risk factors. A subject suspected of having cancer has generally not been tested for cancer. However, a "subject suspected of having cancer" encompasses an individual who has received an initial diagnosis (e.g., a CT scan showing a mass or increased PSA level) but for whom the stage of cancer is not known. The term further includes people who once had cancer (e.g., an individual in remission).

As used herein, the term "subject at risk for cancer" refers to a subject with one or more risk factors for developing a specific cancer. Risk factors include, but are not limited to, gender, age, genetic predisposition, environmental exposure, previous incidents of cancer, preexisting non-cancer diseases, and lifestyle.

As used herein, the term "characterizing cancer in subject" refers to the identification of one or more properties of a cancer sample in a subject, including but not limited to, the presence of benign, pre-cancerous or cancerous tissue, the stage of the cancer, and the subject's prognosis. Cancers may be characterized by the identification of the expression of one or more cancer marker genes, including but not limited to, the cancer markers disclosed herein.

As used herein, the term "characterizing prostate tissue in a subject" refers to the identification of one or more properties of a prostate tissue sample (e.g., including but not limited to, the presence of cancerous tissue, the presence of pre-cancerous tissue that is likely to become cancerous, and the presence of cancerous tissue that is likely to metastasize). In some embodiments, tissues are characterized by the identification of the expression of one or more cancer marker genes, including but not limited to, the cancer markers disclosed herein.

As used herein, the term "cancer marker genes" refers to a gene whose expression level, alone or in combination with other genes, is correlated with cancer or prognosis of cancer. The correlation may relate to either an increased or decreased expression of the gene. For example, the expression of the gene may be indicative of cancer, or lack of expression of the gene may be correlated with poor prognosis in a cancer patient.

As used herein, the term "a reagent that specifically detects expression levels" refers to reagents used to detect the expression of one or more genes (e.g., including but not limited to, the cancer markers of the present invention). Examples of suitable reagents include but are not limited to, nucleic acid probes capable of specifically hybridizing to the gene of interest, PCR primers capable of specifically amplifying the gene of interest, and antibodies capable of specifically binding to proteins expressed by the gene of interest.

As used herein, the term "detecting a decreased or increased expression relative to non-cancerous prostate control" refers to measuring the level of expression of a gene (e.g., the level of mRNA or protein) relative to the level in a non-cancerous prostate control sample. Gene expression can be measured using any suitable method, including but not limited to, those described herein.

As used herein, the term "detecting a change in gene expression (e.g., hepsin, pim-1, EZH2, AMACR, maspin, etc.) in the prostate cell sample in the presence of said test compound relative to the absence of said test compound" refers to measuring an altered level of expression (e.g., increased or decreased) in the presence of a test compound relative to the absence of the test compound.

As used herein, the term "instructions for using said kit for detecting cancer in said subject" includes instructions for using the reagents contained in the kit for the detection and characterization of cancer in a sample from a subject. In some embodiments, the instructions further comprise the statement of intended use required by the U.S. Food and Drug Administration (FDA) in labeling in vitro diagnostic products. The FDA classifies in vitro diagnostics as medical devices and requires that they be approved through the 510(k) procedure. Information required in an application under 510(k) includes: 1) The in vitro diagnostic product name, including the trade or proprietary name, the common or usual name, and the classification name of the device; 2) The intended use of the product; 3) The establishment registration number, if applicable, of the owner or operator submitting the 510(k) submission; the class in which the in vitro diagnostic product was placed under section 513 of the FD&C Act, if known, its appropriate panel, or, if the owner or operator determines that the device has not been classified under such section, a statement of that determination and the basis for the determination that the in vitro diagnostic product is not so classified; 4) Proposed labels, labeling and advertisements sufficient to describe the in vitro diagnostic product, its intended use, and directions for use. Where applicable, photographs or engineering drawings should be supplied; 5) A statement indicating that the device is similar to and/or different from other in vitro diagnostic products of comparable type in commercial distribution in the U.S., accompanied by data to support the statement; 6) A 510(k) summary of the safety and effectiveness data upon which the substantial equivalence determination is based; or a statement that the 510(k) safety and effectiveness information supporting the FDA finding of substantial equivalence will be made available to any person within 30 days of a written request; 7) A statement that the submitter believes, to the best of their knowledge, that all data and information submitted in the premarket notification are truthful and accurate and that no material fact has been omitted; 8) Any additional information regarding the in vitro diagnostic product requested that is necessary for the FDA to make a substantial equivalency determination. Additional information is available at the Internet web page of the US FDA.

As used herein, the term "prostate cancer expression profile map" refers to a presentation of expression levels of genes in a particular type of prostate tissue (e.g., primary, metastatic, and pre-cancerous prostate tissues). The map may be presented as a graphical representation (e.g., on paper or on a computer screen), a physical representation (e.g., a gel or array) or a digital representation stored in computer memory. Each map corresponds to a particular type of prostate tissue (e.g., primary, metastatic, and pre-cancerous) and thus provides a template for comparison to a patient sample. In preferred embodiments, maps are generated from pooled samples comprising tissue samples from a plurality of patients with the same type of tissue.

As used herein, the term "stage of cancer" refers to a qualitative or quantitative assessment of the level of advancement of a cancer. Criteria used to determine the stage of a cancer include, but are not limited to, the size of the tumor, whether the tumor has spread to other parts of the body and where the cancer has spread (e.g., within the same organ or region of the body or to another organ).

As used herein, the term "providing a prognosis" refers to providing information regarding the impact of the presence of cancer (e.g., as determined by the diagnostic methods of the present invention) on a subject's future health (e.g., expected morbidity or mortality, the likelihood of getting cancer, and the risk of metastasis).

As used herein, the term "prostate specific antigen failure" refers to the development of high prostate specific antigen levels in a patient following prostate cancer therapy (e.g., surgery). See Examples 3 and 4 for examples of how prostate specific antigen failure is determined. As used herein, the term "risk of developing prostate specific antigen failure" refers to a subject's relative risk (e.g., the percent chance or a relative score) of developing prostate specific antigen failure following prostate cancer therapy.

As used herein, the term "post surgical tumor tissue" refers to cancerous tissue (e.g., prostate tissue) that has been removed from a subject (e.g., during surgery).

As used herein, the term "subject diagnosed with a cancer" refers to a subject who has been tested and found to have cancerous cells. The cancer may be diagnosed using any suitable method, including but not limited to, biopsy, x-ray, blood test, and the diagnostic methods of the present invention.

As used herein, the term "initial diagnosis" refers to results of initial cancer diagnosis (e.g. the presence or absence of cancerous cells). An initial diagnosis does not include information about the stage of the cancer of the risk of prostate specific antigen failure.

As used herein, the term "biopsy tissue" refers to a sample of tissue (e.g., prostate tissue) that is removed from a subject for the purpose of determining if the sample contains cancerous tissue. In some embodiment, biopsy tissue is obtained because a subject is suspected of having cancer. The biopsy tissue is then examined (e.g., by microscopy) for the presence or absence of cancer.

As used herein, the term "inconclusive biopsy tissue" refers to biopsy tissue for which histological examination has not determined the presence or absence of cancer.

As used herein, the term "gene transfer system" refers to any means of delivering a composition comprising a nucleic acid sequence to a cell or tissue. For example, gene transfer systems include, but are not limited to, vectors (e.g., retroviral, adenoviral, adeno-associated viral, and other nucleic acid-based delivery systems), microinjection of naked nucleic acid, polymer-based delivery systems (e.g., liposome-based and metallic particle-based systems), biolistic injection, and the like. As used herein, the term "viral gene transfer system" refers to gene transfer systems comprising viral elements (e.g., intact viruses, modified viruses and viral components such as nucleic acids or proteins) to facilitate delivery of the sample to a desired cell or tissue. As used herein, the term "adenovirus gene transfer system" refers to gene transfer systems comprising intact or altered viruses belonging to the family Adenoviridae.

As used herein, the term "nucleic acid molecule" refers to any nucleic acid containing molecule, including but not limited to, DNA or RNA. The term encompasses sequences that include any of the known base analogs of DNA and RNA including, but not limited to, 4-acetylcytosine, 8-hydroxy-N-6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragment are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "heterologous gene" refers to a gene that is not in its natural environment. For example, a heterologous gene includes a gene from one species introduced into another species. A heterologous gene also includes a gene native to an organism that has been altered in some way (e.g., mutated, added in multiple copies, linked to non-native regulatory sequences, etc). Heterologous genes are distinguished from endogenous genes in that the heterologous gene sequences are typically joined to DNA sequences that are not found naturally associated with the gene sequences in the chromosome or are associated with portions of the chromosome not found in nature (e.g., genes expressed in loci where the gene is not normally expressed).

As used herein, the term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

The term "wild-type" refers to a gene or gene product isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product that displays modifications in sequence and or functional properties (i.e., altered characteristics) when compared to the wild-type gene or gene product. It is noted that naturally occurring mutants can be isolated; these are identified by the fact that they have altered characteristics (including altered nucleic acid sequences) when compared to the wild-type gene or gene product.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

As used herein, the terms "an oligonucleotide having a nucleotide sequence encoding a gene" and "polynucleotide having a nucleotide sequence encoding a gene," means a nucleic acid sequence comprising the coding region of a gene or in other words the nucleic acid sequence that encodes a gene product. The coding region may be present in a cDNA, genomic DNA or RNA form. When present in a DNA form, the oligonucleotide or polynucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the term "oligonucleotide," refers to a short length of single-stranded polynucleotide chain. Oligonucleotides are typically less than 200 residues long (e.g., between 15 and 100), however, as used herein, the term is also intended to encompass longer polynucleotide chains. Oligonucleotides are often referred to by their length. For example a 24 residue oligonucleotide is referred to as a "24-mer". Oligonucleotides can form secondary and tertiary structures by self-hybridizing or by hybridizing to other polynucleotides. Such structures can include, but are not limited to, duplexes, hairpins, cruciforms, bends, and triplexes.

As used herein, the terms "complementary" or "complementarity" are used in reference to polynucleotides (i.e., a sequence of nucleotides) related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "homology" refers to a degree of complementarity. There may be partial homology or complete homology (i.e., identity). A partially complementary sequence is a nucleic acid molecule that at least partially inhibits a completely complementary nucleic acid molecule from hybridizing to a target nucleic acid is "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous nucleic acid molecule to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that is substantially non-complementary (e.g., less than about 30% identity); in the absence of non-specific binding the probe will not hybridize to the second non-complementary target.

When used in reference to a double-stranded nucleic acid sequence such as a cDNA or genomic clone, the term "substantially homologous" refers to any probe that can hybridize to either or both strands of the double-stranded nucleic acid sequence under conditions of low stringency as described above.

A gene may produce multiple RNA species that are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the T.sub.m of the formed hybrid, and the G:C ratio within the nucleic acids. A single molecule that contains pairing of complementary nucleic acids within its structure is said to be "self-hybridized."

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m = 81.5 + 0.41(\% \text{ G+C})$, when a nucleic acid is in aqueous solution at 1 M NaCl (See e.g., Anderson and Young, Quantitative Filter Hybridization, in Nucleic Acid Hybridization [1985]). Other references include more sophisticated computations that take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. Those skilled in the art will recognize that "stringency" conditions may be altered by varying the parameters just described either individually or in concert. With "high stringency" conditions, nucleic acid base pairing will occur only between nucleic acid fragments that have a high frequency of complementary base sequences (e.g., hybridization under "high stringency" conditions may occur between homologs with about 85-100% identity, preferably about 70-100% identity). With medium stringency conditions, nucleic acid base pairing will occur between nucleic acids with an intermediate frequency of complementary base sequences (e.g., hybridization under "medium stringency" conditions may occur between homologs with about 50-70% identity). Thus, conditions of "weak" or "low" stringency are often required with nucleic acids that are derived from organisms that are genetically diverse, as the frequency of complementary sequences is usually less.

"High stringency conditions" when used in reference to nucleic acid hybridization comprise conditions equivalent to binding or hybridization at 42 C in a solution consisting of 5×SSPE (43.8 g/l NaCl, 6.9 g/l NaH$_2$PO$_4$H$_2$O and 1.85 g/l EDTA, pH adjusted to 7.4 with NaOH), 0.5% SDS, 5×Denhardt's reagent and 100 µg/ml denatured salmon sperm DNA followed by washing in a solution comprising 0.1×SSPE, 1.0% SDS at 42 C when a probe of about 500 nucleotides in length is employed.

"Medium stringency conditions" when used in reference to nucleic acid hybridization comprise conditions equivalent to binding or hybridization at 42 C in a solution consisting of 5×SSPE (43.8 g/l NaCl, 6.9 g/l NaH$_2$PO$_4$H$_2$O and 1.85 g/l EDTA, pH adjusted to 7.4 with NaOH), 0.5% SDS, 5×Denhardt's reagent and 100 µg/ml denatured salmon sperm DNA followed by washing in a solution comprising 1.0×SSPE, 1.0% SDS at 42 C when a probe of about 500 nucleotides in length is employed.

"Low stringency conditions" comprise conditions equivalent to binding or hybridization at 42 C in a solution consisting of 5×SSPE (43.8 g/l NaCl, 6.9 g/l NaH$_2$PO$_4$H$_2$O and 1.85 g/l EDTA, pH adjusted to 7.4 with NaOH), 0.1% SDS, 5×Denhardt's reagent [50×Denhardt's contains per 500 ml: 5 g Ficoll (Type 400, Pharamcia), 5 g BSA (Fraction V; Sigma)] and 100 g/ml denatured salmon sperm DNA followed by washing in a solution comprising 5×SSPE, 0.1% SDS at 42 C when a probe of about 500 nucleotides in length is employed.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.) (see definition above for "stringency").

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

As used herein, the term "amplifiable nucleic acid" is used in reference to nucleic acids that may be amplified by any amplification method. It is contemplated that "amplifiable nucleic acid" will usually comprise "sample template."

As used herein, the term "sample template" refers to nucleic acid originating from a sample that is analyzed for the presence of "target." In contrast, "background template" is used in reference to nucleic acid other than sample template that may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

As used herein, the term "primer" refers to an oligonucleotide, whether occurring naturally as in a purified restriction digest or produced synthetically, that is capable of acting as a point of initiation of synthesis when placed under conditions in which synthesis of a primer extension product that is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, that is capable of hybridizing to at least a portion of another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein the term "portion" when in reference to a nucleotide sequence (as in "a portion of a given nucleotide sequence") refers to fragments of that sequence. The fragments may range in size from four nucleotides to the entire nucleotide sequence minus one nucleotide (10 nucleotides, 20, 30, 40, 50, 100, 200, etc.).

As used herein, the term "target," refers to the region of nucleic acid bounded by the primers. Thus, the "target" is sought to be sorted out from other nucleic acid sequences. A "segment" is defined as a region of nucleic acid within the target sequence.

As used herein, the term "polymerase chain reaction" ("PCR") refers to the method of K. B. Mullis U.S. Pat. Nos. 4,683,195 4,683,202, and 4,965,188, hereby incorporated by reference, which describe a method for increasing the concentration of a segment of a target sequence in a mixture of genomic DNA without cloning or purification. With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process are, themselves, efficient templates for subsequent PCR amplifications.

As used herein, the terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

As used herein, the term "amplification reagents" refers to those reagents (deoxyribonucleotide triphosphates, buffer, etc.), needed for amplification except for primers, nucleic acid template and the amplification enzyme. Typically, amplification reagents along with other reaction components are placed and contained in a reaction vessel (test tube, microwell, etc.).

The terms "in operable combination," "in operable order," and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "isolated" when used in relation to a nucleic acid, as in "an isolated oligonucleotide" or "isolated polynucleotide" refers to a nucleic acid sequence that is identified and separated from at least one component or contaminant with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may be single-stranded), but may contain both the sense and anti-sense strands (i.e., the oligonucleotide or polynucleotide may be double-stranded).

As used herein, the term "purified" or "to purify" refers to the removal of components (e.g., contaminants) from a sample. For example, antibodies are purified by removal of contaminating non-immunoglobulin proteins; they are also purified by the removal of immunoglobulin that does not bind to the target molecule. The removal of non-immunoglobulin proteins and/or the removal of immunoglobulins that do not bind to the target molecule results in an increase in the percent of target-reactive immunoglobulins in the sample. In another example, recombinant polypeptides are expressed in bacterial host cells and the polypeptides are purified by the removal of host cell proteins; the percent of recombinant polypeptides is thereby increased in the sample.

"Amino acid sequence" and terms such as "polypeptide" or "protein" are not meant to limit the amino acid sequence to the complete, native amino acid sequence associated with the recited protein molecule.

The term "native protein" as used herein to indicate that a protein does not contain amino acid residues encoded by vector sequences; that is, the native protein contains only those amino acids found in the protein as it occurs in nature. A native protein may be produced by recombinant means or may be isolated from a naturally occurring source.

As used herein the term "portion" when in reference to a protein (as in "a portion of a given protein") refers to fragments of that protein. The fragments may range in size from four amino acid residues to the entire amino acid sequence minus one amino acid.

The term "Southern blot," refers to the analysis of DNA on agarose or acrylamide gels to fractionate the DNA according to size followed by transfer of the DNA from the gel to a solid support, such as nitrocellulose or a nylon membrane. The immobilized DNA is then probed with a labeled probe to detect DNA species complementary to the probe used. The DNA may be cleaved with restriction enzymes prior to electrophoresis. Following electrophoresis; the DNA may be partially depurinated and denatured prior to or during transfer to the solid support. Southern blots are a standard tool of molecular biologists (J. Sambrook et al., Molecular Cloning: A Laboratory Manual, Cold Spring Harbor Press, NY, pp 9.31 9.58 [1989]).

The term "Northern blot," as used herein refers to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (J. Sambrook, et al., supra, pp 7.39 7.52 [1989]).

The term "Western blot" refers to the analysis of protein(s) (or polypeptides) immobilized onto a support such as nitrocellulose or a membrane. The proteins are run on acrylamide gels to separate the proteins, followed by transfer of the protein from the gel to a solid support, such as nitrocellulose or a nylon membrane. The immobilized proteins are then exposed to antibodies with reactivity against an antigen of interest. The binding of the antibodies may be detected by various methods, including the use of radiolabeled antibodies.

The term "transgene" as used herein refers to a foreign gene that is placed into an organism by, for example, introducing the foreign gene into newly fertilized eggs or early embryos. The term "foreign gene" refers to any nucleic acid (e.g., gene sequence) that is introduced into the genome of an animal by experimental manipulations and may include gene sequences found in that animal so long as the introduced gene does not reside in the same location as does the naturally occurring gene.

As used herein, the term "vector" is used in reference to nucleic acid molecules that transfer DNA segment(s) from one cell to another. The term "vehicle" is sometimes used interchangeably with "vector." Vectors are often derived from plasmids, bacteriophages, or plant or animal viruses.

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The terms "overexpression" and "overexpressing" and grammatical equivalents, are used in reference to levels of mRNA to indicate a level of expression approximately 3-fold higher (or greater) than that observed in a given tissue in a control or non-transgenic animal. Levels of mRNA are measured using any of a number of techniques known to those skilled in the art including, but not limited to Northern blot analysis. Appropriate controls are included on the Northern blot to control for differences in the amount of RNA loaded from each tissue analyzed (e.g., the amount of 28S rRNA, an abundant RNA transcript present at essentially the same amount in all tissues, present in each sample can be used as a means of normalizing or standardizing the mRNA-specific signal observed on Northern blots). The amount of mRNA present in the band corresponding in size to the correctly spliced transgene RNA is quantified; other minor species of RNA which hybridize to the transgene probe are not considered in the quantification of the expression of the transgenic mRNA.

The term "fusion protein" as used herein refers to a protein formed by expression of a hybrid gene made by combining two gene sequences. Typically this is accomplished by cloning a cDNA into an expression vector in frame with an existing gene. The fusion partner may act as a reporter (e.g., βgal) or may provide a tool for isolation purposes (e.g., GST).

Suitable systems for production of recombinant proteins include but are not limited to prokaryotic (e.g., *Escherichia coli*), yeast (e.g., *Saccaromyces cerevisiae*), insect (e.g., baculovirus), mammalian (e.g., Chinese hamster ovary), plant (e.g., safflower), and cell-free systems (e.g., rabbit reticulocyte).

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "calcium phosphate co-precipitation" refers to a technique for the introduction of nucleic acids into a cell. The uptake of nucleic acids by cells is enhanced when the nucleic acid is presented as a calcium phosphate-nucleic acid co-precipitate. The original technique of Graham and van der Eb (Graham and van der Eb, Virol., 52:456 [1973]), has been modified by several groups to optimize conditions for particular types of cells. The art is well aware of these numerous modifications.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA.

As used herein, the term "selectable marker" refers to the use of a gene that encodes an enzymatic activity that confers the ability to grow in medium lacking what would otherwise be an essential nutrient (e.g. the HIS3 gene in yeast cells); in addition, a selectable marker may confer resistance to an antibiotic or drug upon the cell in which the selectable marker is expressed. Selectable markers may be "dominant"; a dominant selectable marker encodes an enzymatic activity that can be detected in any eukaryotic cell line. Examples of dominant selectable markers include the bacterial aminoglycoside 3' phosphotransferase gene (also referred to as the neo gene) that confers resistance to the drug G418 in mammalian cells, the bacterial hygromycin G phosphotransferase (hyg) gene that confers resistance to the antibiotic hygromycin and the bacterial xanthine-guanine phosphoribosyl transferase gene (also referred to as the gpt gene) that confers the ability to grow in the presence of mycophenolic acid. Other selectable markers are not dominant in that their use must be in conjunction with a cell line that lacks the relevant enzyme activity. Examples of non-dominant selectable markers include the thymidine kinase (tk) gene that is used in conjunction with tk.sup.– cell lines, the CAD gene that is used in conjunction with CAD-deficient cells and the mammalian hypoxanthine-guanine phosphoribosyl transferase (hprt) gene that is used in conjunction with hprt.sup.– cell lines. A review of the use of selectable markers in mammalian cell lines is provided in Sambrook, J. et al., Molecular Cloning: A Laboratory Manual, 2nd ed., Cold Spring Harbor Laboratory Press, New York (1989) pp. 16.9 16.15.

As used herein, the term "cell culture" refers to any in vitro culture of cells. Included within this term are continuous cell lines (e.g., with an immortal phenotype), primary cell cultures, transformed cell lines, finite cell lines (e.g., non-transformed cells), and any other cell population maintained in vitro.

As used, the term "eukaryote" refers to organisms distinguishable from "prokaryotes." It is intended that the term encompass all organisms with cells that exhibit the usual characteristics of eukaryotes, such as the presence of a true nucleus bounded by a nuclear membrane, within which lie the chromosomes, the presence of membrane-bound organelles, and other characteristics commonly observed in eukaryotic organisms. Thus, the term includes, but is not limited to such organisms as fungi, protozoa, and animals (e.g., humans).

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

The terms "test compound" and "candidate compound" refer to any chemical entity, pharmaceutical, drug, and the like that is a candidate for use to treat or prevent a disease, illness, sickness, or disorder of bodily function (e.g., cancer). Test compounds comprise both known and potential therapeutic compounds. A test compound can be determined to be therapeutic by screening using the screening methods of the present invention. In some embodiments of the present invention, test compounds include antisense compounds.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, crystals and industrial samples. Such examples are not however to be construed as limiting the sample types applicable to the present invention.

As used herein, "proliferating" and "proliferation" refer to cells undergoing mitosis. Similarly, the "growth state" of a cell refers to the rate of proliferation of the cell and/or the state of differentiation of the cell. An "altered growth state" is a growth state characterized by an abnormal rate of proliferation (e.g., a cell exhibiting an increased or decreased rate of proliferation relative to a normal cell).

In some embodiments, the present invention provides methods and compositions for "retarding growth of cancer cell," whereby different aspects of cancer cell growth are inhibited. As used herein, the term "retarding growth" indicates that the methods and compositions of the present invention inhibit proliferation of a cancer cell. In preferred embodiments, the "retarding growth" indicates that DNA replication (e.g., as measured by BrdU or tritiated thymidine incorporation) is at least 10% less than that observed in untreated or control-treated cancer cells. In particularly preferred embodiments, the term "retarding growth" indicates that DNA replication is at least 25% less than that observed in untreated or control-treated cancer cells. In still further preferred embodiments, the term "retarding growth" indicates that DNA replication is at least 50% (e.g., 75%, 90%, 95% or 99%) less than that observed in untreated or control-treated cancer cells.

In some preferred embodiments, the term "retarding growth" indicates that the methods and compositions of the present invention induce death (e.g., apoptosis) of a cancer cell. In preferred embodiments, the "retarding growth" indicates that apoptosis (e.g., as measured by FACS analysis and BrdU incorporation or any other suitable method) is at least 10% greater than that observed in untreated or control-treated cancer cells. In particularly preferred embodiments, the term "retarding growth" indicates that apoptosis is at least 25% greater than that observed in untreated or control-treated cancer cells. In still further preferred embodiments, the term "retarding growth" indicates that apoptosis is at least 50% (e.g., 75%, 90%, 95% or 99%) greater than that observed in untreated or control-treated cancer cells.

The term "control" refers to subjects or samples that provide a basis for comparison to experimental subjects or samples. For instance, the use of control subjects or samples permits determinations to be made regarding the efficacy of experimental procedures. In some embodiments, the term "control subject" refers to animals, which receive a mock treatment (e.g., vehicle alone).

As used herein, the terms "gene transfer" and "transfer of genetic information" refer to the process of moving a gene or genes from one place to another. In preferred embodiments of the present invention, the term "gene transfer" refers to the transfer of a polynucleotide to cells and/or tissues of an animal to achieve a therapeutic effect. In some embodiments, the polynucleotide may be in the form of a plasmid, a gene fragment or an oligonucleotide. In some embodiments, "gene transfer" is temporary or transient, in other embodiments "gene transfer" is sustained, and in still further embodiments, the gene transfer is long-lived, permanent or stable.

The terms "sample" and "specimen" in the present specification and claims are used in their broadest sense. On the one hand, they are meant to include a specimen or culture. On the other hand, they are meant to include both biological and environmental samples. In preferred embodiments, the term "sample" refers to biopsy material obtained from a subject's pancreas.

The term "carcinoma" refers to a malignant new growth made up of epithelial cells tending to infiltrate surrounding tissues and to give rise to metastases. Exemplary carcinomas include: "basal cell carcinoma", which is an epithelial tumor of the skin that, while seldom metastasizing, has potentialities for local invasion and destruction; "squamous cell carcinoma", which refers to carcinomas arising from squamous epithelium and having cuboid cells; "carcinosarcoma", which include malignant tumors composed of carcinomatous and sarcomatous tissues; "adenocystic carcinoma", carcinoma marked by cylinders or bands of hyaline or mucinous stroma separated or surrounded by nests or cords of small epithelial cells, occurring in the mammary and salivary glands, and mucous glands of the respiratory tract; "epidermoid carcinoma", which refers to cancerous cells that tend to differentiate in the same way as those of the epidermis (e.g., tend to form prickle cells and undergo cornification); "nasopharyngeal carcinoma", which refers to a malignant tumor arising in the epithelial lining of the space behind the nose; and "renal cell carcinoma", which pertains to carcinoma of the renal parenchyma composed of tubular cells in varying arrangements. However, in preferred embodiments of the present invention, the term "carcinoma" refers to "adenocarcinoma," which is a malignant tumor originating in glandular epithelium.

The terms "epithelia", "epithelial" and "epithelium" refer to the cellular covering of internal and external body surfaces (cutaneous, mucous and serous), including the glands and other structures derived therefrom (e.g., corneal, esophegeal, epidermal, and hair follicle epithelial cells).

The term "overexpression" as used in reference to gene expression levels means any level of gene expression in cells of a tissue that is higher than the normal level of expression for that tissue. The normal level of expression for a tissue is assessed by measuring gene expression in a healthy portion of the tissue of interest.

The term "prodrug" is intended to encompass compounds that, under physiological conditions, are converted into the therapeutically active agents of the present invention. A common method for making a prodrug is to include selected moieties that are hydrolyzed under physiological conditions to reveal the desired molecule. In other embodiments, the prodrug is converted by an enzymatic activity of the host animal.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "antisense molecule" refers to polynucleotides and oligonucleotides capable of binding to an mRNA molecule. In particular, an antisense molecule is a DNA or RNA sequence complementary to an mRNA sequence of interest. In preferred embodiments, the term β-catenin antisense molecule refers to a single-stranded DNA or RNA sequence that binds to at least a portion of a β-catenin mRNA molecule to form a duplex which then blocks further transcription and/or translation.

The term "RNA interference" or "RNAi" refers to the silencing or decreasing of gene expression by iRNA or siRNAs. It is the process of sequence-specific, post-transcriptional gene silencing in animals and plants, initiated by iRNA that is homologous in its duplex region to the sequence of the silenced gene. The gene may be endogenous or exogenous to the organism, present integrated into a chromosome or present in a transfection vector that is not integrated into the genome. The expression of the gene is either completely or partially inhibited. RNAi may also be considered to inhibit the function of a target RNA; the function of the target RNA may be complete or partial.

The term "interfering RNA (iRNA)" refers to a double stranded RNA molecule that mediates RNA interference (RNAi). At least one strand of the duplex or double-stranded region of an iRNA is substantially homologous to or substantially complementary to a target RNA molecule. The strand complementary to a target RNA molecule is the "antisense strand;" the strand homologous to the target RNA molecule is the "sense strand," and is also complementary to the iRNA antisense strand. iRNAs may also contain additional sequences; non-limiting examples of such sequences include linking sequences, or loops, as well as stem and other folded structures.

The iRNA can serve as a source of siRNA. siRNAs generally comprise a duplex, or double-stranded region, of about 18-25 nucleotides long; often siRNAs contain from about two to four unpaired nucleotides at the 3' end of each strand. At least one strand of the duplex or double-stranded region of a siRNA is substantially homologous to or substantially complementary to a target RNA molecule. The strand complementary to a target RNA molecule is the "antisense strand;" the strand homologous to the target RNA molecule is the "sense strand," and is also complementary to the siRNA antisense strand. siRNAs may also contain additional sequences; non-limiting examples of such sequences include linking sequences, or loops, as well as stem and other folded structures. siRNAs appear to function as key intermediaries in triggering RNA interference in invertebrates and in vertebrates, and in triggering sequence-specific RNA degradation during posttranscriptional gene silencing in plants.

The term "target RNA molecule" refers to an RNA molecule to which at least one strand of the short double-stranded region of an iRNA is homologous or complementary. Typically, when such homology or complementary is about 100%, the siRNA is able to silence or inhibit expression of the target RNA molecule. Although it is believed that processed mRNA is a target of siRNA, the present invention is not limited to any particular hypothesis, and such hypotheses are not necessary to practice the present invention. Thus, it is contemplated that other RNA molecules may also be targets of siRNA. Such targets include unprocessed mRNA, ribosomal RNA, and viral RNA genomes.

GENERAL DESCRIPTION OF THE INVENTION

A mechanistic link between inflammation and tumor promotion dependent on NF-κB has been established. Now as described herein a new inflammation-activated signaling pathway controlling prostate cancer metastasis has been identified. Defective activation of IκB kinase α (IKKα) inhibits distant organ metastasis in TRAMP mice, which express SV40 T antigen in the prostate epithelium. Decreased metastasis correlated with elevated expression of the metastasis suppressor maspin, whose ablation restored metastatic activity. IKKα activation, which can be triggered by receptor activator of NF-κB (RANK), whose ligand is expressed by tumor-infiltrating inflammatory cells, elevates metastatic activity and represses maspin gene transcription through a novel NF-κB-independent mechanism requiring nuclear translocation of IKKα. Nuclear IKKα correlates with the degree of progression in mouse and human prostate cancers and links inflammatory signaling to metastasis.

DETAILED DESCRIPTION OF THE INVENTION

A mechanistic link between inflammation and tumor promotion has recently been established[1]. Activation of NF-κB by the IKK complex in epithelial cells inhibits apoptotic elimination of pre-neoplastic cells, whereas NF-κB in inflammatory cells provides emerging tumors with paracrine growth factors[2-4]. These mechanisms promote early tumor development and progression. Inflammation enhances growth of transplanted cancers via NF-κB-dependent mechanisms[5] and NF-κB was proposed to promote metastasis by inhibiting apoptosis[6] and through epithelial to mesenchymal transition (EMT)[7]. However before development of the present invention whether and how inflammation can promote metastatic spread of spontaneous primary cancer (as opposed to transplanted tumors) had not been critically evaluated. Whereas localized primary cancer can be surgically removed or radio-ablated, distant site metastases in liver, lung, lymph nodes or bone, are the most deadly complication of cancer, accounting for 90% of cancer-related deaths[8]. A better mechanistic understanding of metastatic cancer spread is a pre-requisite for development of anti-metastatic therapies.

NF-κB activation depends on the IκB kinase (IKK) complex, which contains two catalytic subunits: IKKα and IKKβ[11, 12]. Gene ablation experiments have revealed a major role for IKKβ in NF-κB activation and in linking inflammation to cancer via NF-κB-dependent mechanisms[13]. By comparison, the function of IKKα is versatile, including NF-κB-independent control of keratinocyte differentiation[14] and attenuation of NF-κB activation during inflammation and its resolution[15]. IKKα also activates the alternative NF-κB signaling pathway in immune cells[16] and the classical NF-κB pathway in mammary epithelial cells[17]. In the latter case, IKKα is activated upon occupancy of RANK by RANK ligand (RANKL), leading to induction of cyclin D1 transcription and proliferation of lobuloalveolar epithelial cells during pregnancy[17].

Mammary gland development in females is controlled by sex steroids, estrogen and progesterone. Similarly, proliferation of the prostate epithelium depends on testosterone[18]. Given these similarities, the question of whether IKKα activity is also required for development of the prostate gland and emergence of CaP was examined. Ikkα$^{AA/AA}$ mice, in which IKKα activation is prevented by replacement of two critical serine residues in its activation loop with two alanine residues[17], exhibit normal prostate development and form CaP in response to a prostate-specific SV40 T antigen (Tag) transgene. These mice however, were found to display very few distant organ metastases. As described herein, this observation led to the identification of a new signaling pathway that depends on IKKα enzymatic activity and translocation to the nucleus, but is independent of NF-κB. This pathway represses expression of the metastasis-suppressor gene maspin[19, 20] and can be triggered by occupancy of RANK, whose ligand is produced by tumor-infiltrating inflammatory cells. Nuclear IKKα translocation also correlates with clinical progression in human CaP.

In recent years it has become clear that inflammation and a pro-inflammatory microenvironment make important and critical contributions to tumor development[1, 39, 40]. Mechanistic studies have revealed an important tumor promoting role for the inflammation-responsive IKK complex and its target NF-κB, acting both within cancer (or pre-malignant) cells and inflammatory cells[13]. Although inflammation is also expected to enhance tumor progression and metastasis, distinct genetically-established mechanisms linking inflammation and metastasis were not well defined. As described in more detail in the experimental examples a novel mechanism specifically promotes prostate cancer metastasis through IKKα activation inducible upon binding of the proinflammatory cytokine RANKL to its receptor RANK.

Homozygosity for a mutation that prevents IKKα activation in a mouse model of prostate cancer driven by SV40 Tag, results in a dramatic decrease in number of metastases. Although the mutation also reduces the growth rates of primary cancer, its most pronounced effect was on metastatogenesis in organs such as lymph nodes and liver. Furthermore, a specific requirement for IKKα kinase activity was seen in two distinct and widely accepted assays of metastatic potential: injection of prostate carcinoma cells into the spleen and their metastatic growth in the liver and the chick embryo spontaneous metastasis assay. Inactivation of IKKα had only a marginal effect on the tumorigenic potential of these cells.

Analysis of known genes that promote or suppress metastasis[24] revealed that IKKα exerted its pro-metastatic effect by repressing transcription of the maspin gene. Inactivation of IKKα increased maspin expression and inhibited metastasis, whereas siRNA-mediated maspin knockdown elevated the metastatic potential of Ikkα$^{AA/AA}$ CaP cells to the level of WT CaP cells. Repression of maspin expression required nuclear translocation of catalytically active IKKα. Importantly, an excellent correlation between the amount of active nuclear IKKα, the level of maspin expression and the stage of cancer progression was observed in both the TRAMP mouse model and as well as human prostate cancer.

The maspin gene encodes a member of the serpin family with well established anti-metastatic activity in breast and prostate cancers[20, 25, 31]. An excellent inverse correlation between maspin expression and metastatic potential of CaP in human patients was observed, such that metastatic CaPs express little or no maspin[29, 41]. It was observed that in metastatic human CaP, the maspin promoter and 5' control region are heavily methylated and that treatment with DNA methyl transferase (DNMT) inhibitors reactivated maspin transcription[42]. Yet, how maspin transcription is repressed prior to epigenetic silencing was heretofore unknown. Based on a general model in which DNMTs are recruited to gene regulatory regions through interactions with specific repressors or co-repressors, whose repressive action may be transient[43], the initial repression of maspin transcription has been determined to be mediated by IKKα activation (e.g., in response to engagement of RANK or similar receptors). With time, this transient repression is converted to epigenetic silencing through DNA methylation, thereby committing CaP cells to a metastatic fate.

Although maspin is a member of the serpin family, the mechanism by which it suppresses metastatic activity is not fully understood[20, 31]. Among other observations, it was shown that maspin controls cell migration and invasion by increasing cell-extracellular matrix adhesion through interaction with β1 integrin[45]. This could explain the anti-metastatic activity of maspin and the effect of RANK activation on prostate and mammary carcinoma cell motility[44].

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: N (normal); M (molar); mM (millimolar); μM (micromolar); mol (moles); mmol (millimoles); μmol (micromoles); nmol (nanomoles); pmol (picomoles); g (grams); mg (milligrams); μg (micrograms); ng (nanograms); l or L (liters); ml (milliliters); μl (microliters); cm (centimeters); mm (millimeters); μm (micrometers); nm (nanometers); C (degrees Centigrade); PCR (polymerase chain reaction); CaP (prostate cancer); GFP (green fluorescent protein); IKKα(IkB kinase α); PSA (prostate cancer antigen); RANK (receptor activator of NF-kB); TRAMP mice (transgenic mice that express the SV40 T antigen in the prostate epithelium); WT (wild type).

Example 1

Nuclear Cytokine-Activated IKKα Controls Prostate Cancer Metastasis by Repressing Maspin Materials and Methods Animals. Ikkα$^{AA/AA}$ (BL6x129) mice were crossed to TRAMP (BL6) mice[18] to generate Ikkα$^{AA/+}$/TRAMP$^{+/-}$ mice that were intercrossed with Ikkα$^{AA/AA}$ mice for six generations. After that, Ikkα$^{AA/+}$/TRAMP$^{+/-}$ mice were intercrossed to generate Ikkα$^{AA/+}$/TRAMP$^{+/+}$ mice. Ikkα$^{AA/AA}$/TRAMP$^{+/+}$ females were crossed with Ikkα$^{AA/+}$ males to generate Ikkα$^{+/+}$/TRAMP$^{+/-}$ and Ikkα$^{AA/AA}$/TRAMP$^{+/-}$ mice. Only Ikkα$^{AA/AA}$/TRAMP$^{+/-}$ and Ikkα$^{+/+}$/TRAMP$^{+/-}$ male littermates were used in our studies. C57BL6 Nu/Nu mice used for metastasis studies were from the Jackson Laboratory. All mice were maintained under specific pathogen-free conditions and experimental protocols were approved by the UCSD Animal Care Program, following National Institutes of Health guidelines.

Figure 11:
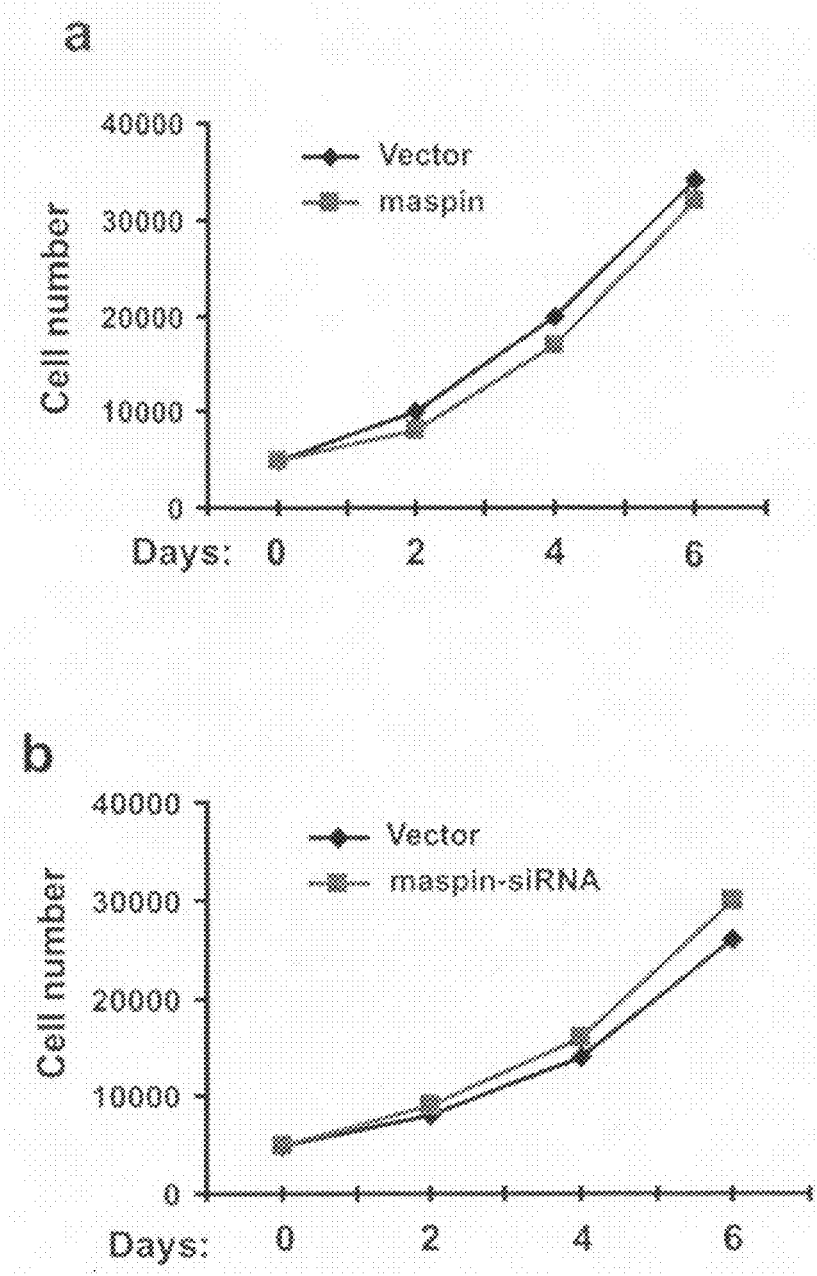

Human material. Anonymous human prostatic normal, benign, and tumor tissue samples, quick-frozen in liquid nitrogen at surgery, were provided by the Cooperative Human Tissue Network (CHTN), Pathology reports were provided by CHTN for each tissue sample and re-confirmed by a pathologist at UCSD (FIG. 11). The TNM (T: Primary tumor, N: Regional lymph nodes, M: Distant metastasis) stage data were also provided by CHTN. Only primary tumor samples were examined. The patients included in this study, 51 to 71 years-old, had not received prior radiation or chemotherapy. The samples were used for frozen sectioning and preparation of nuclear and cytoplasmic protein extracts.

Histological procedures. Prostate and CaP tissues and dissected metastatic tumors were immersed in 10% neutral buffered formalin before sectioning. Sections were stained with Harris haematoxylin and eosin (H&E) and BrdU-positive cells were identified as described[5]. Staining for maspin and E-cadherin (Santa Cruz Biotechnology) was performed using ABC staining kit (Vector Laboratories) according to manufacturer's recommendations. Staining for T cells and macrophages was performed using anti-CD3-FITC (Pharmingen) and anti-F4/80-FITC (Caltag) as described[5].

Cell Culture and retrovirus infection. Normal prostate and CaP were minced and incubated overnight with collagenase [2 mg/ml in RPMI-1640 supplemented with 5% fetal calf serum (FCS)] at 37° C. with shaking. Digests were pipetted and washed once in RPMI-1640 medium with 5% FCS, and centrifuged at 800×g for 5 min. Pellets were resuspended in 0.1% (w/v) trypsin and incubated for 30 min at 37° C. on a shaker. Final digests were washed three times, resuspended, and centrifuged at 360×g for 1 min. Pellets enriched for epithelial or carcinoma cells were resuspended in epithelial cell growth medium[46]. Single cells were obtained by passing the suspension through a 40-mm cell sieve.

The pS2-maspin construct and empty vector were transfected into GP2-HEK293 cells (Clontech) to produce viral particles that were used to infect CaP or epithelial cells in the presence of polybrene. Infected cells were selected in 100 μg/ml zeocin (Invitrogen). siRNA to mouse maspin mRNA was generated as described[45] and cloned into pSUPER.retro-.puro (Oligo Engine) and transfected into GP2-HEK293 cells. Virus-containing supernatants were incubated with CaP cells for 2 days with polybrene and infected cells were selected in 1 µg/ml puromycin.

Metastasis assays. For liver metastasis studies, $2\times10^6$ viable CaP cells in 100 µl PBS were injected into surgically exposed spleens of 6-8 week old Nu/Nu male mice using a tuberculin syringe with a 26 G needle. After 10 min, the major splenic vasculature was ligated and the spleen was removed. Four weeks later, mice were sacrificed and liver metastases were enumerated[47] and level of SV40 Tag mRNA in total liver RNA determined by Q-RT-PCR. Mouse cyclophilin mRNA was used as internal control. The chick embryo metastasis assay was conducted as described[32]. Pulmonary metastases were quantified based on the presence of SV40 Tag DNA within chick lung genomic DNA. The Tag signal was normalized to a GAPDH signal. To approximate the actual number of CaP cells present in each tissue sample, a standard curve was generated through quantitative amplification of genomic DNA extracted from a serial dilution of CaP cells mixed with chick lung homogenates.

Analysis of gene expression. Total tissue RNA was prepared using the RNAeasy kit (Qiagen). Q-RT-PCR was performed as described[5]. Cells or tumor tissues were lysed and analyzed by SDS-PAGE and immunoblotting[5] with antibodies to cyclin A, cyclin B1, cyclin B2, cyclin H, Cdk2, HDAC1, maspin, p38 (all from Santa Cruz Biotechnology), cyclin D, IKKβ (UBI), IKKα (Cell Signaling), IKKγ (Pharmngen), and actin (Sigma).

Luciferase assay. A human maspin-luciferase reporter, pM-759-Luc, was kindly provided by Dr. S. Srivastava, Uniformed Services University. The promoter region of maspin was amplified by PCR according to the reported DNA sequence (Zhang et al., Cell Growth Differ, 8:179-186, 1997). The pM-Luc(-759) was generated by primers GAGACTC-GAGGCTGAAGTACAGTGGTTAG (with the XhoI site) set forth as SEQ ID NO:5 and GAGAAAGCTTAGAAG-CAGCGGTGGCTCACC (with the HindIII site) set forth as SEQ ID NO:6. The ARE-mutant maspin-luciferase reporter was kindly provided by Dr. Z. Khalkhali-Ellis, University of Iowa. The −486, −316, −267, −212, −145 maspin promoter mutants were generated either by PCR or restriction enzyme digests. Reporters and expression vectors were co-transfected with the internal control pRL-TK into Ikkα$^{-/-}$ mouse embryonic fibroblasts (MEFs) using Lipofectamine (Invitrogen). Luciferase activity was measured using the Dual-luciferase reporter assay system (Promega). Results are presented as relative reporter activity after normalization to the internal control pRL-TK.

Chromatin immunoprecipitation. ChIP assays were performed using the Acetyl-Histone H3 Immunoprecipitation Assay kit (Upstate Biotechnology, Charlottesville, Va., USA), according to the manufacturer's instructions with some modifications. Chromatin from $2\times10^6$ human mammary epithelial (HME) cells was sheared by a sonicator by 13×15 sec pulses in 200 µl lysis buffer. The lysate was precleared with Rat IgG and salmon-sperm DNA-saturated protein G Sepharose and then precipitated with HA antibody (Roche, Calif.). Samples were analyzed by PCR. The human maspin promoter and intron 2 regions were amplified with the primer pairs 5'-GCAGAATGAG CTGCTGCAG-3' (SEQ ID NO:1) and 5'-AGAAGCAGCG GTGGCTCACC-3' (SEQ ID NO:2) and 5'-AGGAGCCAGT CAGCATAGGA-3' (SEQ ID NO:3) and 5'-TTTGGCTGCA AACACCTACA-3' (SEQ ID NO:4), respectively.

Kinase assay. IκB kinase activity was measured as described using IκBα (1-67) as a substrate[48].

Statistical analysis. Data were analyzed by Student's t test, Paired t test, Chi-square test, or Kaplan-Meier survival analysis. Data were taken to be significant when p<0.05.

Results

IKKα Activity is Required for Prostate Cancer Metastasis.

Figure 1:
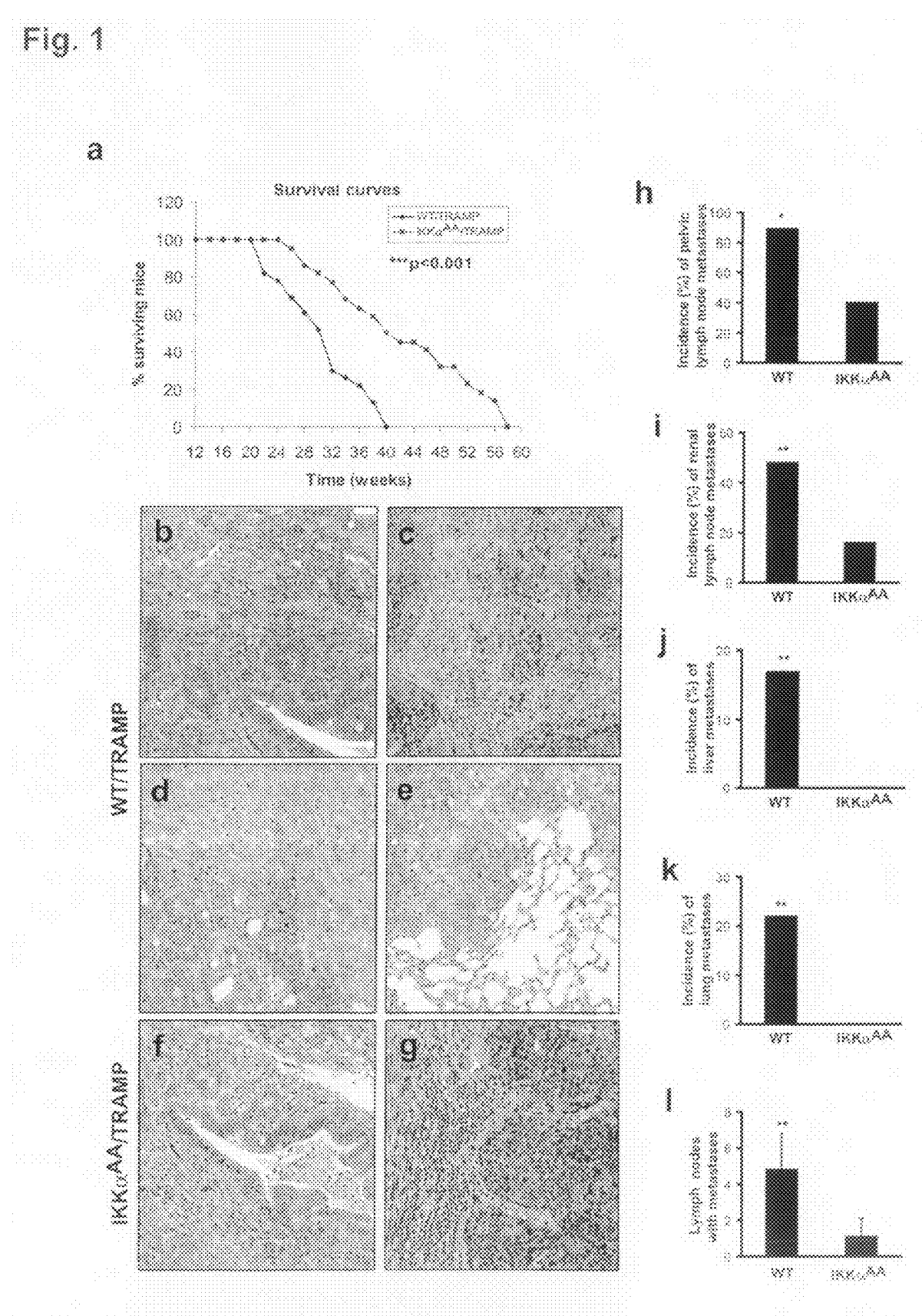
FIG. 1A-L illustrates that IKKα activity is required for prostate cancer (CaP) metastasis. a, TRAMP mice were intercrossed for at least 6 generations with Ikkα$^{AA/AA}$ mice. Survival of Ikkα$^{AA/AA}$/TRAMP and WT/TRAMP mice was compared. In b-g, Histological analysis (H&E staining of paraffin embedded sections; magnification: 200×) WT/TRAMP primary prostate carcinomas (b), and lymph node (c), liver (d), and lung (e) metastases, as well as Ikkα$^{AA/AA}$/TRAMP primary prostate carcinomas (f) and a rare lymph node metastasis (g). h-k, Incidence of pelvic lymph node (h), renal lymph node (i), liver (j) and lung (k) metastases. 1, Average numbers of lymph nodes harboring metastases (WT/TRAMP, n=23; Ikkα$^{AA/AA}$/TRAMP, n=22). *p<0.05, **p<0.01.

Ikkα$^{AA/AA}$ mutant mice were crossed with TRAMP mice expressing SV40 Tag from the prostate specific probasin promoter[18] for at least 6 generations. As previously described[18, 21, 22], WT/TRAMP mice developed CaP rather early and started dying around 22 weeks of age, but homozygocity for the Ikkα$^{AA}$ allele on the same genetic background prolonged tumor onset and delayed mortality (FIG. 1A). Whereas the entire WT/TRAMP cohort succumbed to CaP by 40 weeks of age, 50% of the Ikkα$^{AA/AA}$/TRAMP cohort was still alive at this point. Despite reduced mortality in the Ikkα$^{AA/AA}$/TRAMP group, no discernable histological differences in primary tumors and lymph node metastases were found between the genotypes upon necropsy (FIG. 1B-G). Despite having typical primary CaPs at the time of death whose size was similar to primary CaP in dead WT/TRAMP mice, Ikkα$^{AA/AA}$/TRAMP mice exhibited considerably less distant site metastases (FIG. 1H-L). For instance, 87% (20/23) of dead WT/TRAMP mice had pelvic lymph node metastases (FIG. 1H), 43% (10/23) had renal lymph node metastases (FIG. 1), 17% (4/23) had liver metastases (FIG. 1J) and 22% (5/23) had lung metastases (FIG. 1K). By contrast, only 41% (9/22) of dead Ikkα$^{AA/AA}$/TRAMP mice exhibited pelvic lymph node metastases (FIG. 1H), 18% (4/22) showed renal lymph node metastases (FIG. 1I), and none (0/22) had liver or lung metastases (FIG. 1J-K). The average number of lymph nodes harboring metastases in Ikkα$^{AA/AA}$/TRAMP mice was much lower than in WT/TRAMP mice (FIG. 1L). Consistent with previous observations 22, TRAMP mice of either genotype exhibit very few bone metastases.

IKKα Kinase Activity is not Critical for Early Carcinogenesis.

These findings indicate that IKKα plays a critical role in CaP progression, particularly in metastatic spread. To detect if IKKα affected early prostate carcinogenesis, we compared prostate size, weight, morphology and histology in three month-old male mice. No clear differences in these parameters were found and both genotypes showed similar primary tumor pathology, from high grade PIN to well differentiated CaP (FIG. 2A-B), indicating that IKKα kinase activity is not critical for early prostate carcinogenesis.

As mentioned above, growth of the prostate and mammary epithelia depend on sex steroids and Ikkα$^{AA/AA}$ females exhibit retarded lobuloalveolar epithelial development during pregnancy[17]. We therefore extended the analysis of prostate development to nontransgenic Ikkα$^{AA/AA}$ and WT mice, but found no differences in prostate size, weight, morphology, histology and proliferation rates.

Figure 2:
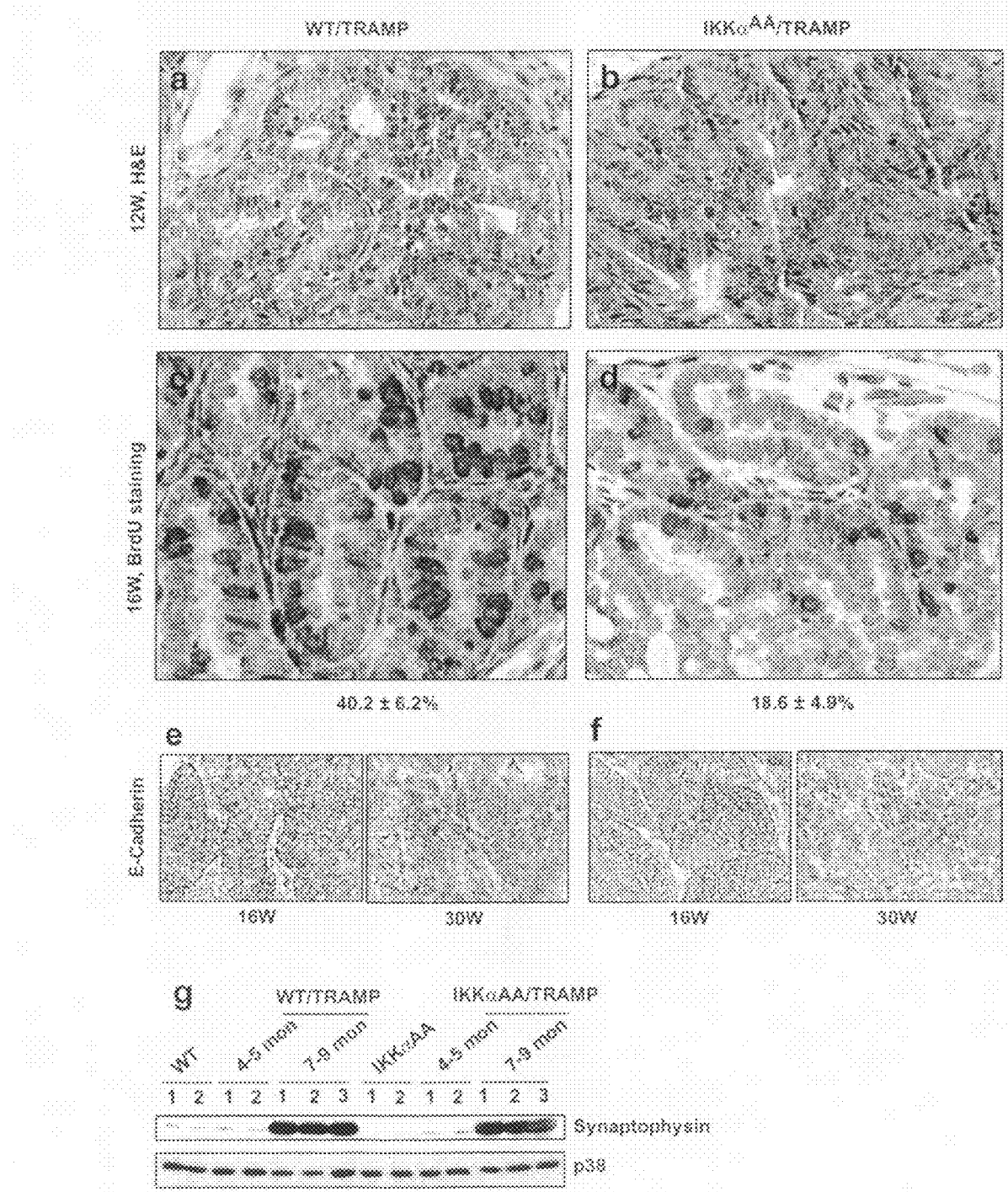
FIG. 2A-G shows that IKKα affects CaP proliferation but not histology. a, b, Histology of prostate adenocarcinomas from 3 months-old WT/TRAMP (a) and Ikkα$^{AA/AA}$/TRAMP (b) mice was examined by H&E staining (magnification: 200×). c, d, Cell proliferation in prostate carcinomas of 4 months-old WT/TRAMP (c) and Ikkα$^{AA/AA}$/TRAMP (d) mice was examined by BrdU labeling. Percentages of BrdU-positive cells are indicated underneath. e, f, Expression of the epithelial marker E-Cadherin was examined by immunohistochemistry in CaP from 16 week and 30 week-old WT/TRAMP (e) and Ikkα$^{AA/AA}$/TRAMP (f) mice. g, Expression of the neuroendocrine marker synaptophysin was examined by immunoblotting of prostate extracts from the indicated mice.

We did, however, identify a proliferation defect in Ikkα$^{AA/AA}$/TRAMP CaP of four-month-old mice. Male mice of either genotype were pulsed with 5-bromodeoxyuridine (BrdU) and BrdU incorporation, which identifies cells undergoing DNA synthesis, was examined 2.5 hrs later. Fewer BrdU-positive cells were present in CaP of Ikkα$^{AA/AA}$/TRAMP mice than in WT/TRAMP CaP (FIG. 2C-D). However, primary tumor burden was similar at time of death in WT/TRAMP and Ikkα$^{AA/AA}$/TRAMP mice, indicating that despite lower growth rates, primary CaP eventually reach the same size in Ikkα$^{AA/AA}$/TRAMP mice as in WT/TRAMP mice and that accelerated proliferation in WT CaPs is partially balanced by increased death.

Progression of CaP in TRAMP mice was shown to correlate with reduced E-cadherin expression, a hallmark of EMT[21]. The same was observed in our mice regardless of their genotype (FIG. 2E-F). CaP progression is also associated with increase expression of the neuroendocrine marker synaptophysin both in human cancer[23] and TRAMP mice[21]. Synoaptophysin expression was indeed elevated in advanced CaP from 7-9 month old mice but was not influenced by the IKKα status (FIG. 2G).

Elevated Maspin Expression in Primary Tumors of Ikkα$^{AA/AA}$/TRAMP Mice.

Tumor metastasis is governed by genetic and epigenetic factors that regulate metastasis-suppressor or metastasis-promoter genes[24]. We compared expression of approximately forty such genes, including E cadherin, in primary CaP of both genotypes by quantitative (Q) RT-PCR (FIG. 8). The only gene that exhibited marked and consistent differences between Ikkα$^{AA/AA}$/TRAMP and WT/TRAMP CaP was maspin, an established tumor metastasis-suppressor (FIG. 3A).

Maspin was identified as a gene expressed by normal mammary epithelial cells but not by mammary carcinoma, whose forced expression can inhibit invasion and motility of breast cancer cell lines[25]. Further studies confirmed that maspin is highly expressed in normal breast epithelial cells and that its expression is frequently decreased in breast cancer cells and completely lost in metastatic carcinoma[19, 26]. Ectopic maspin expression in mammary epithelium inhibits development of lobuloalveolar structures during pregnancy[27], resulting in a phenotype similar to the mammary phenotype of Ikkα$^{AA/AA}$ mice 7. Furthermore, maspin overexpression from a mammary epithelial promoter dramatically decreased metastasis of SV40 Tag-induced mammary carcinoma[28]. Importantly, there are strong inverse correlations between maspin expression and metastatic potential in human CaP[29-31].

We examined maspin expression in prostates of WT/TRAMP and Ikkα$^{AA/AA}$/TRAMP mice during tumor progression. Maspin was similarly expressed in cancerous prostates of both genotypes at 3 months of age (FIG. 9). However, in WT/TRAMP mice maspin expression began to decline in CaP at 4-5 months of age but remained high in Ikkα$^{AA/AA}$/TRAMP CaPs (FIG. 3b). At 7-8 months of age maspin was no longer detected in WT/TRAMP CaP, but primary tumors in Ikkα$^{AA/AA}$/TRAMP mice retained high maspin expression (FIGS. 3A and C). Immunohistochemistry analysis revealed that maspin was highly expressed in cytoplasm and membranes of Ikkα$^{AA/AA}$/TRAMP CaP cells, but was barely detectable or absent in WT/TRAMP CaP cells (FIGS. 3D and E). Consistent with its role as a metastasis-suppressor, maspin gene expression was extinguished in the rare lymph node metastases found in Ikkα$^{AA/AA}$/TRAMP mice (FIG. 3A).

IKKα Activity and Maspin Expression Determine Metastatic Potential of CaP Cells.

Figure 4:
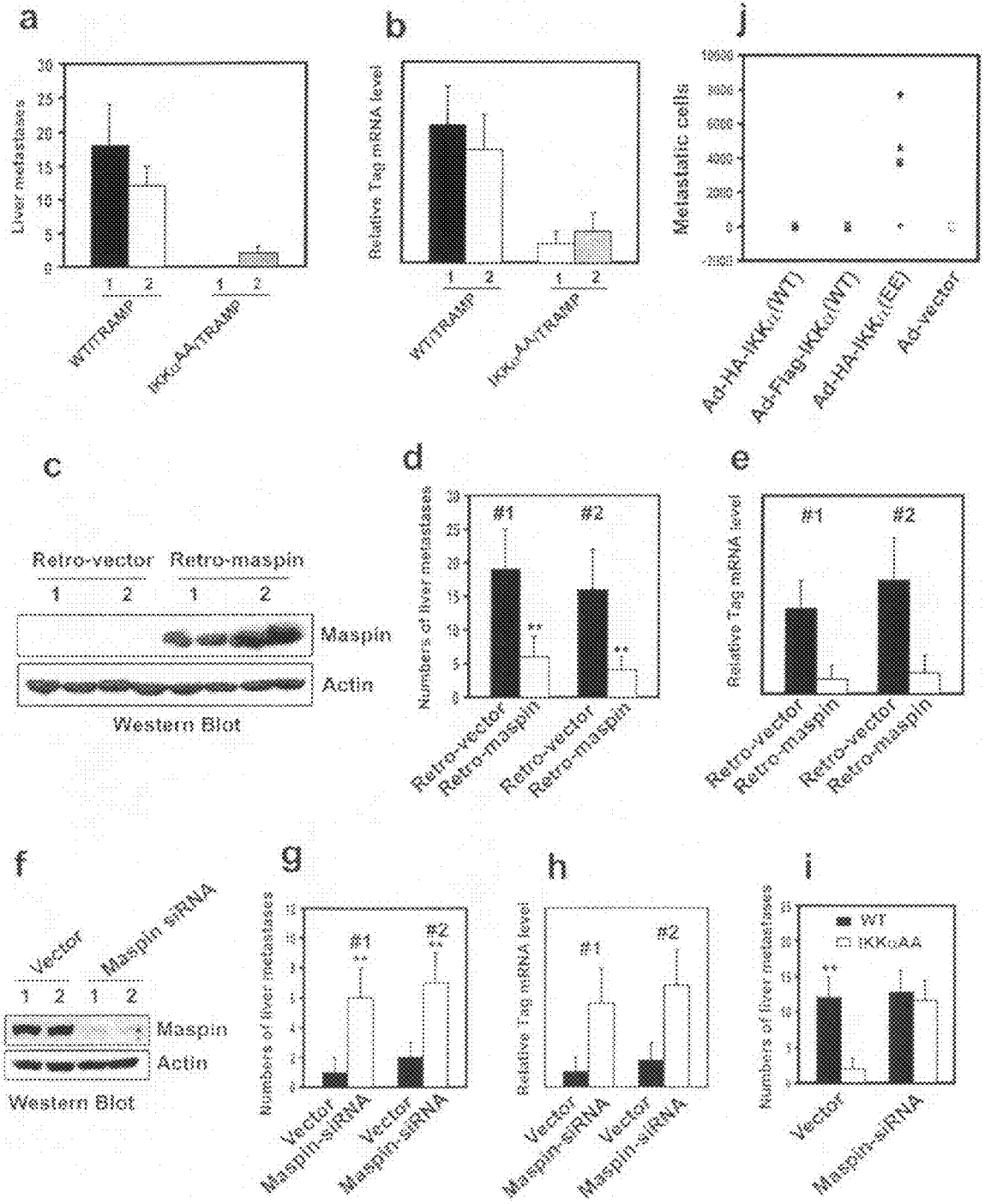
FIG. 4A-J shows that Maspin expression and IKKα activity determine metastatic potential of prostate cancer cells. a, CaP cells from WT/TRAMP and IKKα$^{AA/AA}$/TRAMP mice were isolated and cultured for 1-3 weeks. Single- cell suspensions were injected into spleens of 3-5 Nu/Nu male mice and 10 min later spleens were removed. After 4 weeks mice were sacrificed and liver metastases were counted. Numbers represent different cell isolates and cultures. b, Real-time PCR analysis of SV40 Tag mRNA in livers of Nu/Nu mice whose spleens were inoculated with cultured CaP cells. c, CaP cells from WT/TRAMP mice were infected with either a maspin retrovirus or an 'empty' retrovirus. Two different preparations of transduced cells per virus were selected in 100 μg/ml zeocin for 1 week and immunoblotted for maspin expression. d, Single-cell suspensions of retrovirus-infected and zeocin-selected cells from c were injected into spleens of Nu/Nu male mice and liver metastases were analyzed as in a. e, Real-time PCR analysis of SV40 Tag mRNA in livers from d. f, Primary CaP cells from Ikkα$^{AA/AA}$/TRAMP mice expressing endogenous maspin were infected with maspin siRNA-retrovirus or an "empty" retrovirus vector. Two different preparations of transduced cells per virus were selected in 1 μg/ml puromycin and immunoblotted for maspin expression. g, Single-cell suspensions of retrovirus-infected and puromycin-selected cells from f were injected into spleens of Nu/Nu male mice, and liver metastases were analyzed as in a. h, Real-time PCR of SV40 Tag mRNA in livers from g. i, Maspin was knockdown in WT and Ikkα$^{AA/AA}$ CaP cells and metastatic activity was examined as above. j, Four different coded samples of Ikkα$^{AA/AA}$/TRAMP CaP cells expressing endogenous maspin, infected with the indicated adenoviral vectors were inoculated on the back of the chorioallantoic membrane of a 10-day old chick embryo. After 9 days pulmonary metastasis was quantified by detection of SV40 Tag DNA sequences within chick lung genomic DNA. The chicken GAPDH sequence was used as an internal control.

To determine whether changes in maspin expression account for reduced metastasis in Ikkα$^{AA/AA}$/TRAMP mice we examined metastatic potential of primary CaP cells from 7-8 month old mice that were cultured for 1-3 weeks. Single-cell suspensions were injected into spleens of Nude (Nu/Nu) male mice and 10 min later the spleens were removed. After 4 weeks, metastases to liver were enumerated and liver SV40 Tag mRNA was quantitated. While maspin-negative WT CaP cells gave rise to numerous liver metastases, very few metastases were formed by Ikkα$^{AA/AA}$ CaP cells, which expressed high amounts of maspin (FIG. 4A). Similar results were obtained by Q-PCR analysis of Tag mRNA (FIG. 4B).

By contrast, the tumogenic potential of subcutaneously transplanted Ikkα$^{AA/AA}$ CaP cells was only marginally lower than of WT CaP cells (FIG. 10) and in vitro these cells exhibited nearly identical proliferation rates (FIG. 11).

Next, we examined whether manipulation of maspin expression alters metastatic potential. Primary WT CaP cells were infected with either a maspin-expressing retrovirus or an empty retrovirus control. Transduced cells selected in zeocin for 1 week contained high levels of maspin when infected with the maspin retrovirus (FIG. 4C). Forced maspin expression greatly reduced metastatic ability measured by the same assays described above (FIG. 4D-E). We also knocked-down maspin expression in Ikkα$^{AA/AA}$ CaP cells using a maspin siRNA-retrovirus. After 1 week selection in puromycin, cells receiving maspin siRNA contained much less maspin (FIG. 4F) and displayed substantially higher metastatic potential than mock-infected cells (FIG. 4G-H). Importantly, maspin knockdown increased the metastatic potential of Ikkα$^{AA/AA}$ CaP cells to that of WT CaP cells (FIG. 4I). Thus, differential maspin expression is a major determinant of metastatic potential.

To examine the effect of IKKα activation on metastatic activity we used adenoviral vectors to express either WT or a constitutively active IKKα(EE), in which the activation loop serines were replaced with phosphomimic glutamate residues[16], in Ikkα$^{AA/AA}$ primary CaP cells. Due to the transient nature of adenovirus infection we used the chick embryo spontaneous metastasis assay[32] to determine metastatic activity. This model allows for spontaneous metastatic spread of cancer cells inoculated on the chorioallantoic membrane of 10 days old chicken embryos. Only cells transduced with the IKKα(EE) virus showed metastatic activity in this assay (FIG. 4J). Yet, primary transplanted tumors grew at the same rate. Thus in addition to maspin, IKKα activity also determines metastatic potential.

IKKα Translocates to the Nucleus in Prostate Carcinoma and Inhibits Maspin Transcription.

Next, we examined how IKKα controls maspin gene expression. Primary Ikkα$^{AA/AA}$ CaP cells expressing endogenous maspin were infected with adenoviruses encoding GFP, WT IKKα, activated IKKα(EE) or activated IKKβ(EE). Three days later, maspin protein levels were examined. IKKα (EE) significantly down-regulated maspin expression, while WT IKKα or IKKβ(EE) had little or no effect (FIG. 5A). To examine whether IKKα regulates maspin gene transcription we used a maspin-luciferase reporter containing 759 base pairs (bp) of the 5'-human maspin upstream region[33]. Transfection of the reporter with different amounts of IKKα(EE) expression vector into Ikkα$^{-/-}$ mouse embryonic fibroblasts (MEFs) resulted in dose-dependent repression, an effect not seen with WT IKKα or the inactivateable IKKα(AA) variant (FIG. 5B). No repression of maspin promoter activity was seen upon co-expression of activated IKKβ(EE) (FIG. 5C), which is a more potent activator of NF-κB-dependent transcription than IKKα(EE) (FIG. 12).

We generated human maspin promoter truncation mutants and fused them to a luciferase reporter. These constructs were co-transfected with or without IKKα(EE) expression vector into Ikkα$^{-/-}$ MEFs and luciferase activity was determined. There was a sharp cutoff in responsiveness to IKKα(EE) between 316 and 267 bp of maspin 5' DNA (FIG. 5D). This region of the human maspin promoter contains several putative cis acting elements including an androgen receptor (AR) responsive element (ARE)[34]. Although AR was reported to repress maspin transcription[29, 34, 35], we could not find any effect of castration on mouse maspin expression (FIG. 13) or inactive (unliganded) or activated AR on repression of human maspin promoter by IKKα(EE) (FIG. 14).

Since the transfections were conducted with the human maspin promoter, we used the normal human mammary epithelial HME cells that express maspin to examine whether ectopically introduced activated IKKα interacts with the endogenous maspin promoter in native chromatin. Chromatin immunoprecipitation (ChIP) analysis revealed that activated IKKα was recruited to the endogenous maspin promoter region (FIG. 5E). The interaction was specific as IKKα did not interact with intron 2 of the maspin gene.

Figure 6:
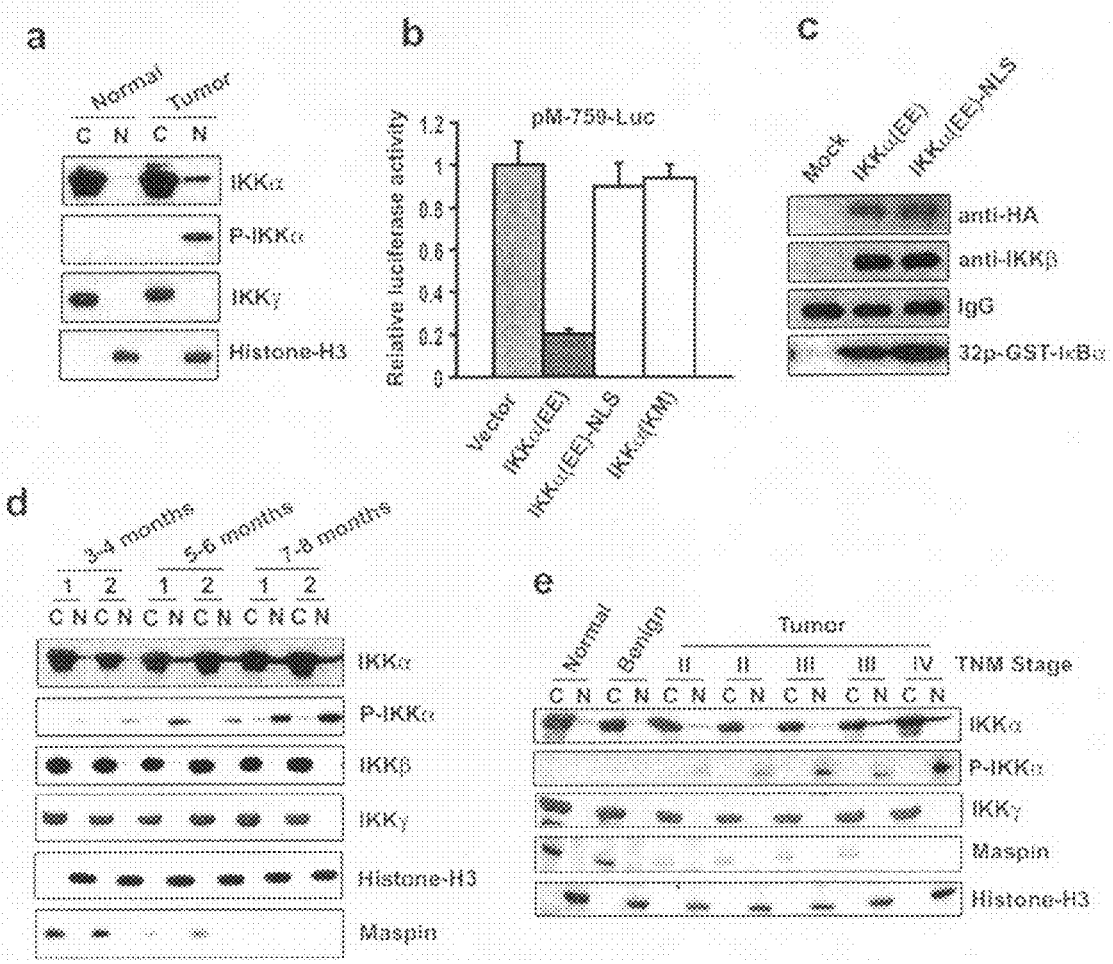
FIG. 6A-E shows that IKKα-mediated repression of Maspin expression requires nuclear entry and kinase activity. a, Nuclear (N) and cytoplasmic (C) extracts of normal and TRAMP prostate epithelium were analyzed for IKKα, phospho(activated)-IKKα, IKKγ and histone H3 by immunoblotting. b, The maspin-luciferase reporter (pM-759-Luc) was co-transfected with empty, IKKα(EE), IKKα(EE)-NLS and IKKα(KM) vectors and luciferase activity was measured as described above. c, HEK293 cells were transfected with different expression vectors as indicated. After 36 hrs IKK complexes were immunoprecipitated with HA-specific antibody and their IκB kinase activity and IKKβ content were measured. d, CaP cells from TRAMP mice of the indicated age (1 and 2 are individual mice) were fractionated into cytoplasmic (C) and nuclear (N) extracts that were examined for IKKα, phospho-IKKα, IKKβ, IKKγ, histone H3 and maspin by immunoblotting. e, Normal human prostate, benign prostatic hyperplasia and prostate tumors at different stages of progression (TNM stage) were divided into nuclear (N) and cytoplasmic (C) fractions that were examined for presence of the indicated proteins by immunoblotting.

We noticed that endogenous IKKα was present in both the cytoplasmic and nuclear fractions of CaP cells, whereas IKKβ and the IKKγ/NEMO regulatory subunit were exclusively cytoplasmic (FIGS. 6A and D). Very little, if any, nuclear IKKα was found in normal prostate epithelium and immunoblotting with phospho-specific antibody revealed that nuclear IKKα in CaP was mostly in its phosphorylated and activated form. While these results are consistent with presence of a nuclear localization sequence (NLS) in IKKα, it is noteworthy that nuclear IKKα was previously found only in differentiating keratinocytes 36. To examine whether IKKα acts in the nucleus to control maspin expression, the maspin-luciferase reporter (pM-759-Luc) was co-transfected with IKKα(EE), IKKα(EE)-NLS (a nuclear localization defective version of activated IKKα) and IKKα(KM) (a catalytically inactive mutant of IKKα) expression vectors into Ikkα$^{-/-}$ MEFs. Neither IKKα(EE)-NLS nor IKKα(KM) repressed maspin promoter activity (FIG. 6B). To exclude the possibility that IKKα(EE)-NLS lost its kinase activity, IKKα (EE)-NLS or IKKα(EE) was expressed in HEK293 cells and their IκB kinase activity was measured. IKKα(EE)-NLS was as active as IKKα(EE) in IκB phosphorylation (FIG. 6C). Hence, the ability of IKKα to repress maspin transcription requires kinase activity and nuclear entry. NF-κB activation depends on IκB phosphorylation in the cytoplasm, and IKKβ (EE), which is a more potent activator of NF-κB than IKKα (EE) (FIG. 12), did not repress maspin expression. Thus repression of maspin by IKKα is NF-κB independent.

The presence of IKKα in the nucleus correlated with the state of CaP progression. The amount of activated nuclear IKKα was substantially higher in CaP from 7-8 month-old WT/TRAMP mice than in CaP from younger mice (FIG. 6D). Furthermore, the amount of IKKα in the nucleus was inversely correlated with maspin expression. Most importantly, the presence of activated nuclear IKKα correlated with clinical grade in human CaP and was highest in stage 4 tumors that did not express maspin (FIG. 6E). No activated IKKα was detected in the nuclear fraction of normal human prostate or benign prostate hyperplasia, whose cytoplasmic fractions contained high levels of maspin.

Tumor-infiltrating Inflammatory Cells Express RANKL, an Inhibitor of Maspin Expression.

Figure 7:
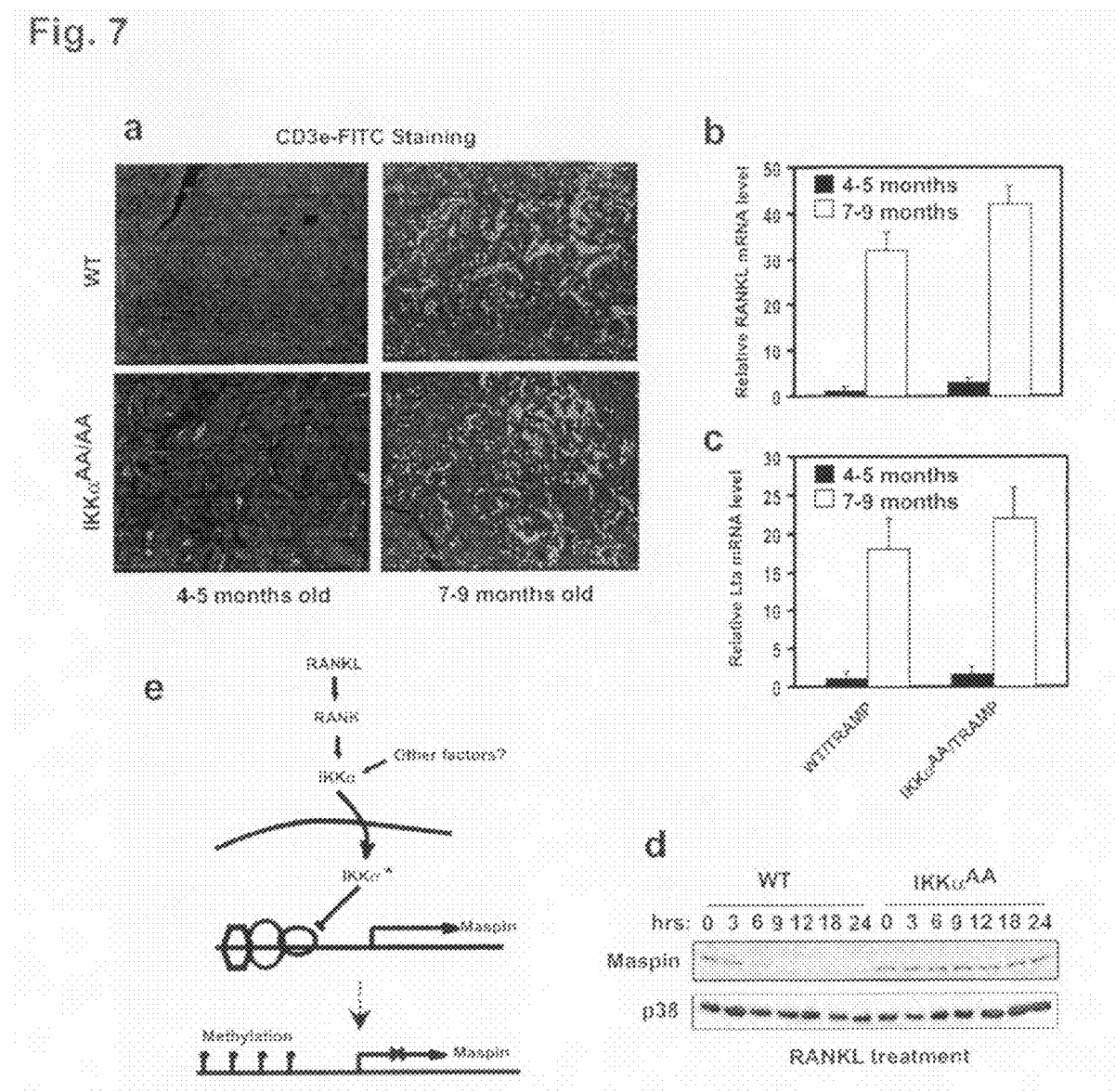

In mammary epithelial cells[17] as well as myeloid cells[37,38] IKKα is activated upon occupancy of RANK by RANKL. Another cytokine that activates IKKα is lymphotoxin (LT) αβ[37]. These members of the tumor necrosis factor (TNF) family are expressed by activated lymphoid and myeloid cells. Immunohistochemistry revealed only small amounts of such cells in early CaP of either genotype, but the amount of tumor infiltrating T cells (CD3$^+$) and macrophages (F4/80$^+$) was dramatically increased in primary prostate tumors of 7-9 month old TRAMP mice (FIG. 7A). Likewise, the levels of RANKL and LTα mRNA were dramatically elevated in CaP from 7-9 month-old TRAMP mice relative to tumors of 4-5 month-old mice (FIG. 7B).

Given the very high increase of RANKL mRNA, which was also seen at the protein level, we treated primary prostate epithelial cells with RANKL and examined maspin expression. Maspin amounts declined within 6 hrs of RANKL application to WT cells but no effect was seen in Ikkα$^{AA/AA}$ cells (FIG. 7D). These results indicate that prostate cancer metastasis could be a consequence of tumor infiltration by RANKL-expressing inflammatory cells that activate IKKα in nuclei of carcinoma cells to repress maspin transcription (FIG. 7E).

REFERENCES

1. Karin, M. & Greten, F. R. NF-κB: linking inflammation and immunity to cancer development and progression. *Nat Rev Immunol* 5, 749-59 (2005).
2. Greten, F. R. et al. IKKβ links inflammation and tumorigenesis in a mouse model of colitis-associated cancer. *Cell* 118, 285-96 (2004).
3. Maeda, S., Kamata, H., Luo, J. L., Leffert, H. & Karin, M. IKKβ couples hepatocyte death to cytokine-driven compensatory proliferation that promotes chemical hepatocarcinogenesis. *Cell* 121, 977-90 (2005).
4. Pikarsky, E. et al. NF-κB functions as a tumour promoter in inflammation-associated cancer. *Nature* 431, 461-466 (2004).
5. Luo, J. L., Maeda, S., Hsu, L. C., Yagita, H. & Karin, M. Inhibition of NF-κB in cancer cells converts inflammation-induced tumor growth mediated by TNFα to TRAIL-mediated tumor regression. *Cancer Cell* 6, 297-305 (2004).
6. Mehlen, P. & Puisieux, A. Metastasis: a question of life or death. *Nat Rev Cancer* 6, 449-58 (2006).
7. Huber, M. A. et al. NF-κB is essential for epithelial-mesenchymal transition and metastasis in a model of breast cancer progression. *J. Clin. Invest.* 114, 569-81 (2004).
8. Weigelt, B., Peterse, J. L. & van't Veer, L. J. Breast cancer metastasis: markers and models. *Nat Rev Cancer* 5, 591-602 (2005).
9. DeMarzo, A. M., Nelson, W. G., Isaacs, W. B. & Epstein, J. I. Pathological and molecular aspects of prostate cancer. *Lancet* 361, 955-64 (2003).
10. Montironi, R., Mazzucchelli, R., Scarpelli, M., Lopez-Beltran, A. & Mikuz, G. Prostate carcinoma I: prognostic factors in radical prostatectomy specimens and pelvic lymph nodes. *BJU Int.* 97, 485-91 (2006).
11. Ghosh, S. & Karin, M. Missing pieces in the NF-κB puzzle. *Cell* 109 Suppl, S81-96 (2002).
12. Rothwarf, D. M. & Karin, M. The NF-κB activation pathway: a paradigm in information transfer from membrane to nucleus. *Sci STKE* 1999, RE1 (1999).
13. Karin, M. Nuclear factor-KB in cancer development and progression. *Nature* 441, 431-6 (2006).
14. Hu, Y. et al. IKKα controls formation of the epidermis independently of NF-κB. *Nature* 410, 710-4 (2001).
15. Lawrence, T., Bebien, M., Liu, G. Y., Nizet, V. & Karin, M. IKKα limits macrophage NF-κB activation and contributes to the resolution of inflammation. *Nature* 434, 1138-1143 (2005).
16. Senftleben, U. et al. Activation by IKKα of a second, evolutionary conserved, NF-κB signaling pathway. *Science* 293, 1495-9 (2001).
17. Cao, Y. et al. IKKα provides an essential link between RANK signaling and cyclin D1 expression during mammary gland development. *Cell* 107, 763-75 (2001).
18. Greenberg, N. M. et al. Prostate cancer in a transgenic mouse. *Proc Natl Acad Sci USA* 92, 3439-43 (1995).

19. Shi, H. Y. et al. Modeling human breast cancer metastasis in mice: maspin as a paradigm. *Histol. Histopathol.* 18, 201-6 (2003).
20. Chen, E. I. & Yates, J. R. Maspin and tumor metastasis. *IUBMB Life* 58, 25-9 (2006).
21. Kaplan-Lefko, P. J. et al. Pathobiology of autochthonous prostate cancer in a pre-clinical transgenic mouse model. *Prostate* 55, 219-37 (2003).
22. Gingrich, J. R. et al. Metastatic prostate cancer in a transgenic mouse. *Cancer Res.* 56, 4096-102 (1996).
23. Chuang, C. K., Wu, T. L., Tsao, K. C. & Liao, S. K. Elevated serum chromogranin A precedes prostate-specific antigen elevation and predicts failure of androgen deprivation therapy in patients with advanced prostate cancer. *J Formos. Med. Assoc.* 102, 480-5 (2003).
24. Steeg, P. S. Metastasis suppressors alter the signal transduction of cancer cells. *Nat Rev Cancer* 3, 55-63 (2003).
25. Zou, Z. et al. Maspin, a serpin with tumor-suppressing activity in human mammary epithelial cells. *Science* 263, 526-9 (1994).
26. Zhang, M. Multiple functions of maspin in tumor progression and mouse development. *Front. Biosci.* 9, 2218-26 (2004).
27. Zhang, M. et al. Maspin plays an important role in mammary gland development. *Dev. Biol.* 215, 278-87 (1999).
28. Zhang, M., Shi, Y., Magit, D., Furth, P. A. & Sager, R. Reduced mammary tumor progression in WAP-Tag/WAP-maspin bitransgenic mice. *Oncogene* 19, 6053-8 (2000).
29. Zou, Z. et al. Maspin expression profile in human prostate cancer (CaP) and in vitro induction of Maspin expression by androgen ablation. *Clin. Cancer Res.* 8, 1172-7 (2002).
30. Cher, M. L. et al. Maspin expression inhibits osteolysis, tumor growth, and angiogenesis in a model of prostate cancer bone metastasis. *Proc Natl Acad Sci USA* 100, 7847-52 (2003).
31. Lockett, J., Yin, S., Li, X., Meng, Y. & Sheng, S. Tumor suppressive maspin and epithelial homeostasis. *J Cell. Biochem.* 97, 651-60 (2006).
32. Stupack, D. G. et al. Potentiation of neuroblastoma metastasis by loss of caspase-8. *Nature* 439, 95-9 (2006).
33. Zou, Z. et al. p53 regulates the expression of the tumor suppressor gene maspin. *J. Biol. Chem.* 275, 6051-4 (2000).
34. Bailey, C. M. et al. Mammary serine protease inhibitor (Maspin) binds directly to interferon regulatory factor 6: identification of a novel serpin partnership. *J. Biol. Chem.* 280, 34210-7 (2005).
35. Zhang, M., Magit, D. & Sager, R. Expression of maspin in prostate cells is regulated by a positive ets element and a negative hormonal responsive element site recognized by androgen receptor. *Proc Natl Acad Sci USA* 94, 5673-8 (1997).
36. Sil, A. K., Maeda, S., Sano, Y., Roop, D. R. & Karin, M. IκB kinase-α acts in the epidermis to control skeletal and craniofacial morphogenesis. *Nature* 428, 660-4 (2004).
37. Bonizzi, G. et al. Activation of IKKα target genes depends on recognition of specific κB binding sites by RelB:p52 dimers. *EMBO J.* 23, 4202-10 (2004).
38. Ruocco, M. G. et al. IκB kinase (IKK)β, but not IKKα, is a critical mediator of osteoclast survival and is required for inflammation-induced bone loss. *J. Exp. Med.* 201, 1677-87 (2005).
39. Balkwill, F., Charles, K. A. & Mantovani, A. Smoldering and polarized inflammation in the initiation and promotion of malignant disease. *Cancer Cell* 7, 211-217 (2005).
40. Coussens, L. M. & Werb, Z. Inflammation and cancer. *Nature* 420, 860-7 (2002).
41. Pierson, C. R. et al. Maspin is up-regulated in premalignant prostate epithelia. *Prostate* 53, 255-62 (2002).
42. Sato, N., Fukushima, N., Matsubayashi, H. & Goggins, M. Identification of maspin and S100P as novel hypomethylation targets in pancreatic cancer using global gene expression profiling. *Oncogene* 23, 1531-8 (2004).
43. Di Croce, L. et al. Methyltransferase recruitment and DNA hypermethylation of target promoters by an oncogenic transcription factor. *Science* 295, 1079-82 (2002).
44. Jones, D. H. et al. Regulation of cancer cell migration and bone metastasis by RANKL. *Nature* 440, 692-6 (2006).
45. Latha, K., Zhang, W., Cella, N., Shi, H. Y. & Zhang, M. Maspin mediates increased tumor cell apoptosis upon induction of the mitochondrial permeability transition. *Mol. Cell. Biol.* 25, 1737-48 (2005).
46. Lang, S. H., Clarke, N. W., George, N. J., Allen, T. D. & Testa, N. G. Interaction of prostate epithelial cells from benign and malignant tumor tissue with bone-marrow stroma. *Prostate* 34, 203-13 (1998).
47. Morimoto-Tomita, M., Ohashi, Y., Matsubara, A., Tsuiji, M. & Irimura, T. Mouse colon carcinoma cells established for high incidence of experimental hepatic metastasis exhibit accelerated and anchorage-independent growth. *Clin. Exp. Metastasis* 22, 513-21 (2005).
48. Zandi, E., Rothwarf, D. M., Delhase, M., Hayakawa, M. & Karin, M. The IκB kinase complex (IKK) contains two kinase subunits, IKKα and IKKβ, necessary for IκB phosphorylation and NF-κB activation. *Cell* 91, 243-252 (1997).

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention, which are obvious to those skilled in the relevant fields, are intended to be within the scope of the following claims.

We claim:

1. A method for detecting the presence of prostate cancer in a subject, comprising:

a) providing a prostate tumor cell sample from a subject, b) detecting the presence or absence of an increased level of phosphorylated, nuclear IKKα (SEQ ID NO: 8) in said prostate tumor cell sample, relative to the level of phosphorylated, nuclear IKKα (SEQ ID NO: 8) in a normal cell sample, wherein an increased level of phosphorylated, nuclear IKKα (SEQ ID NO: 8) in said prostate tumor sample indicates the presence of a cancer selected from the group consisting of prostate carcinoma and metastatic prostate cancer, and the absence of phosphorylated, nuclear IKKα (SEQ ID NO: 8) in said prostate tumor cell sample indicates benign prostatic hyperplasia, and c) detecting the presence or absence of a reduced level of Maspin (SEQ ID NO: 10) in said prostate tumor cell sample relative to the level of Maspin (SEQ ID NO: 10) in a normal cell sample, wherein a reduced level of Maspin (SEQ ID NO: 10) in said prostate tumor sample indicates the presence of a cancer selected from the group consisting of prostate cancer and metastatic prostate cancer.

2. The method of claim 1, wherein said increased level of phosphorylated, nuclear IKKα (SEQ ID NO: 8) in said prostate tumor sample indicates the presence of prostate carcinoma.

3. The method of claim 1, wherein said increased level of phosphorylated, nuclear IKKα (SEQ ID NO: 8) in said prostate tumor sample indicates the presence of metastatic prostate cancer.

4. The method of claim 1, wherein said absence of phosphorylated, nuclear IKKα (SEQ ID NO: 8 in said prostate tumor cell sample indicates benign prostatic hyperplasia.

5. The method of claim 1, wherein said reduced level of Maspin (SEQ ID NO: 10) indicates the presence of prostate cancer.

6. The method of claim 1, wherein said reduced level of Maspin (SEQ ID NO: 10) indicates the presence of metastatic prostate cancer.

7. A method for distinguishing between normal prostate and prostate cancer in a subject, comprising:

a) providing a prostate cell sample from a subject, and b) detecting the presence or absence of an increased level of phosphorylated, nuclear IKKα (SEQ ID NO: 8) in said prostate cell sample, relative to the level of phosphorylated, nuclear IKKα (SEQ ID NO: 8) in a normal cell sample, wherein an increased level of phosphorylated, nuclear IKKα (SEQ ID NO: 8) in said prostate sample indicates the presence of a cancer selected from the group consisting of prostate carcinoma and metastatic prostate cancer.

* * * * *